United States Patent
Marshall et al.

(10) Patent No.: US 9,102,986 B2
(45) Date of Patent: Aug. 11, 2015

(54) **PRIMER AND PROBE SEQUENCES FOR DETECTING *CHLAMYDIA TRACHOMATIS***

(75) Inventors: Ronald L. Marshall, San Diego, CA (US); Shiaolan Y. Ho, Wilmette, IL (US)

(73) Assignee: Abbott Molecular Inc., Des Plaines, IL (US)

(*) Notice: Subject to any disclaimer, the term of this patent is extended or adjusted under 35 U.S.C. 154(b) by 901 days.

(21) Appl. No.: 12/099,622

(22) Filed: Apr. 8, 2008

(65) Prior Publication Data

US 2008/0299567 A1 Dec. 4, 2008

Related U.S. Application Data

(60) Provisional application No. 60/911,684, filed on Apr. 13, 2007.

(51) Int. Cl.
*C12Q 1/68* (2006.01)
*C07H 21/04* (2006.01)

(52) U.S. Cl.
CPC ........................... *C12Q 1/689* (2013.01)

(58) Field of Classification Search
None
See application file for complete search history.

(56) References Cited

U.S. PATENT DOCUMENTS

| | | | |
|---|---|---|---|
| 4,948,882 | A | 8/1990 | Ruth |
| 5,210,015 | A | 5/1993 | Gelfand |
| 5,424,414 | A | 6/1995 | Mattingly |
| 5,464,746 | A | 11/1995 | Fino |
| 5,618,674 | A | 4/1997 | Sanchez-Pescador et al. |
| 5,627,030 | A | 5/1997 | Pandian |
| 2004/0091870 | A1 | 5/2004 | Pabich et al. |
| 2005/0227257 | A1 | 10/2005 | Abravaya et al. |

FOREIGN PATENT DOCUMENTS

| | | |
|---|---|---|
| EP | 1396538 | 3/2004 |
| WO | WO9220702 | 11/1992 |
| WO | WO 9947706 A1 * | 9/1999 |
| WO | WO 0173129 A2 * | 10/2001 |

OTHER PUBLICATIONS

Heid, C.A. et al. Genome Research 6:986-994 (1996).*
Applied Biosystems, "Designing TaqMan MGB Probe and Primer Sets for Allelic Discrimination Assays Using Primer Express Software Version 2.0," 15 pages (2002).*
PCT/US08/59675. International Search Report (PCT Article 18 and Rules 43 and 44) dated Sep. 24, 2008 (4 pp).
Unemo, M., P. Olcen, I. Agne-Stadling, A. Feldt, M. Jurstrand, B. Herrmann, K. Persson, P. Nilsson, T. Ripa, and H. Fredlund. 2007. Experiences with the new genetic variant of *Chlamydia trachomatis* in Orebro county, Sweden—proportion, characteristics and effective diagnostic solution in an emergent situation. Euro Surveill. 12:E5-6.
Genbank Accesion No. X06707 Apr. 27, 1999 *Chlamydia trachomatis* cryptic plasmid pLGV440.
Genbank Accession No. EF121757 Dec. 16, 2006 *Chlamydia trachomatis* plasmid pLGV440 sequence flanking a deletion.
Pickett, M.A., J.S. Everson, P.J. Pead, and I.N. Clarke. 2005. The plasmids of *Chlamydia trachomatis* and *Chlamydophila pneumoniae* (N16): accurate determination of copy number and the paradoxical effect of plasmid-curing agents. Microbiology. 151:893-903.
Black, C.M., J.E. Johnson, C.E. Farshy, T.M. Brown, and B.P. Berdal. 1991. Antigenic variation among strains of *Chlamydia pneumoniae*. J Clin Microbiol. 29:1312-6.
Comanducci, M., S. Ricci, R. Cevenini, and G. Ratti. 1990. Diversity of the *Chlamydia trachomatis* common plasmid in biovars with different pathogenicity. Plasmid. 23:149-54.
Jalal, H., H. Stephen, M.D. Curran, J. Burton, M. Bradley, and C. Carne. 2006. Development and validation of a rotor-gene real-time PCR assay for detection, identification, and quantification of *Chlamydia trachomatis* in a single reaction. J Clin Microbiol. 44:206-13.
Marras, S.A., F.R. Kramer, and S. Tyagi. 1999. Multiplex detection of single-nucleotide variations using molecular beacons. Genet Anal. 14:151-6.
Ngeow, Y.F. 1996. Limitations of serodiagnosis in chlamydial genital tract infections. Ann Acad Med Singapore. 25:300-4.
Nielsen, P.E., M. Egholm, R.H. Berg, and O. Buchardt. 1991. Sequence-selective recognition of DNA by strand displacement with a thymine-substituted polyamide. Science. 254:1497-500.
Palmer, L., and S. Falkow. 1986. A common plasmid of *Chlamydia trachomatis*. Plasmid. 16:52-62.
Ripa, T., and P. Nilsson. 2006. A variant of *Chlamydia trachomatis* with deletion in cryptic plasmid: implications for use of PCR diagnostic tests. Euro Surveill. 11:E061109 2.
Tam, J.E., C.H. Davis, R.J. Thresher, and P.B. Wyrick. 1992. Location of the origin of replication for the 7.5-kb *Chlamydia trachomatis* plasmid. Plasmid. 27:231-6.
Tyagi, S., D.P. Bratu, and F.R. Kramer. 1998. Multicolor molecular beacons for allele discrimination. Nat Biotechnol. 16:49-53.
van der Krol, A.R., J.N. Mol, and A.R. Stuitje. 1988. Modulation of eukaryotic gene expression by complementary RNA or DNA sequences. Biotechniques. 6:958-76.
Zon, G. 1988. Oligonucleotide analogues as potential chemotherapeutic agents. Pharm Res. 5:539-49.
Jaton, K. et al., "A novel real-time PCR to detect *Chlamydia trachomatis* in first-void urine or genital swabs," J. med. Microbiol. (2006) 55:1667-1674.
Koenig, M.G. et al., "Direct comparison of the BD ProbeTec ET system with in-house LightCycler PCR assays for detection of *Chlamydia trachomatis* and *Neisseria gonorrhoeae* from clinical specimens," J. Clin. Microbiol. (2004) 42 (12):5751-5756.
Marshall, R. et al., "Characteristics of the m2000 automated sample preparation and multiplex real-time PCR system for detection of *Chlamydia trachomatis* and *Neisseria gonorrhoeae*," J. Clin. Microbiol. (2007) 45(3):747-751.
Stephens, R.S. et al., "Genome sequence of an obligate intracellular pathogen of humans: *Chlamydia trachomatis*," Science (1998) 282:754-759.

* cited by examiner

*Primary Examiner* — Diana B Johannsen
(74) *Attorney, Agent, or Firm* — Lisa V. Mueller; Michael Best & Friedrich LLP

(57) ABSTRACT

The present invention relates to primers and probes that can be used in various assays to detect a new strain of *Chlamydia trachomatis*. The invention further provides for the simultaneous detection of other diseases, especially *Neisseria gonorrhoeae*.

8 Claims, No Drawings

```
                          SEQUENCE LISTING

<160> NUMBER OF SEQ ID NOS: 44

<210> SEQ ID NO 1
<211> LENGTH: 26
<212> TYPE: DNA
<213> ORGANISM: Artificial
<220> FEATURE:
<223> OTHER INFORMATION: Forward primer (CP2512_2537) for Chlamydia
      detection

<400> SEQUENCE: 1
caagcttaga tccgtttctc atacgg                                        26

<210> SEQ ID NO 2
<211> LENGTH: 28
<212> TYPE: DNA
<213> ORGANISM: Artificial
<220> FEATURE:
<223> OTHER INFORMATION: reverse primer (CP 2624_2651) for Chlamydia
      detection

<400> SEQUENCE: 2
gcaatagaaa cggagatcta cgcaatgg                                      28

<210> SEQ ID NO 3
<211> LENGTH: 27
<212> TYPE: DNA
<213> ORGANISM: Artificial
<220> FEATURE:
<223> OTHER INFORMATION: Probe for Chlamydia detection

<400> SEQUENCE: 3
cctcgatgat ttgagcgtgt gtagcgc                                       27

<210> SEQ ID NO 4
<211> LENGTH: 377
<212> TYPE: DNA
<213> ORGANISM: Chlamydia trachomatis

<400> SEQUENCE: 4
aagttagacg aaattttgtc tttgcgcaca gacgatctat tttttgcatc caatcagatt    60
tcctttcgca ttaaaaaaag acagaataaa gaaaccaaaa ttctaatcac atttcctatc   120
agcttaatgg aggagttgca aaaatacact tgtgggagaa atgggagagt atttgtttct   180 aaaatanggga ttcctgtaac aacaagtcag gttgcgcata attttaggct tgcagagttc   240
tatagtgcta tgaaaataaa aattactcct agagtacttc gtgcaagcgc tttgattcat   300
ttaaagcaaa taggattaaa agatgaggaa atcatgcgta tttcctgtct tcatcgaga   360 caaagtgtgt gttctta                                                 377

<210> SEQ ID NO 5
```

```
<211> LENGTH: 27
<212> TYPE: DNA
<213> ORGANISM: Chlamydia trachomatis

<400> SEQUENCE: 5
ccttcattat gtcggagtct gagcacc                                            27

<210> SEQ ID NO 6
<211> LENGTH: 26
<212> TYPE: DNA
<213> ORGANISM: Chlamydia trachomatis

<400> SEQUENCE: 6
cttcattatg tcggagtctg agcacc                                             26

<210> SEQ ID NO 7
<211> LENGTH: 24
<212> TYPE: DNA
<213> ORGANISM: Chlamydia trachomatis

<400> SEQUENCE: 7
gtcggagtct gagcaccta ggcg                                                24

<210> SEQ ID NO 8
<211> LENGTH: 27
<212> TYPE: DNA
<213> ORGANISM: Chlamydia trachomatis

<400> SEQUENCE: 8
cacagcggtt gctcgaagca cgtgcgg                                            27

<210> SEQ ID NO 9
<211> LENGTH: 24
<212> TYPE: DNA
<213> ORGANISM: Chlamydia trachomatis

<400> SEQUENCE: 9
agcggttgct cgaagcacgt gcgg                                               24

<210> SEQ ID NO 10
<211> LENGTH: 26
<212> TYPE: DNA
<213> ORGANISM: Chlamydia trachomatis

<400> SEQUENCE: 10
caagagtaca tcggtcaacg aagagg                                             26

<210> SEQ ID NO 11
<211> LENGTH: 25
<212> TYPE: DNA
<213> ORGANISM: Chlamydia trachomatis

<400> SEQUENCE: 11
cggcttggga agagcttttg cggcg                                              25

<210> SEQ ID NO 12
<211> LENGTH: 19
<212> TYPE: DNA
<213> ORGANISM: Chlamydia trachomatis

<400> SEQUENCE: 12
gggaagagct tttgcggcg                                                     19
```

```
<210> SEQ ID NO 13
<211> LENGTH: 27
<212> TYPE: DNA
<213> ORGANISM: Chlamydia trachomatis

<400> SEQUENCE: 13
cgtatctcgg gttaatgttg catgatg                                              27

<210> SEQ ID NO 14
<211> LENGTH: 24
<212> TYPE: DNA
<213> ORGANISM: Chlamydia trachomatis

<400> SEQUENCE: 14
cgtatctcgg gttaatgttg catg                                                 24

<210> SEQ ID NO 15
<211> LENGTH: 23
<212> TYPE: DNA
<213> ORGANISM: Chlamydia trachomatis

<400> SEQUENCE: 15
cattgtactc attaaacgag cgg                                                  23

<210> SEQ ID NO 16
<211> LENGTH: 28
<212> TYPE: DNA
<213> ORGANISM: Chlamydia trachomatis

<400> SEQUENCE: 16 gtcaagccctt cccttttatac gctcaagc                                           28

<210> SEQ ID NO 17
<211> LENGTH: 28
<212> TYPE: DNA
<213> ORGANISM: Chlamydia trachomatis

<400> SEQUENCE: 17
ggtggggtta aggcaaatcg cccgcacg                                             28

<210> SEQ ID NO 18
<211> LENGTH: 30
<212> TYPE: DNA
<213> ORGANISM: Chlamydia trachomatis

<400> SEQUENCE: 18
gccttaaccc caccattttt ccggagcgag                                           30

<210> SEQ ID NO 19
<211> LENGTH: 28
<212> TYPE: DNA
<213> ORGANISM: Chlamydia trachomatis

<400> SEQUENCE: 19
ccccaccatt tttccggagc gagttacg                                             28

<210> SEQ ID NO 20
<211> LENGTH: 28
<212> TYPE: DNA
<213> ORGANISM: Chlamydia trachomatis

<400> SEQUENCE: 20
gacaagctta gatccgtttc tcatacgg                                             28
```

```
<210> SEQ ID NO 21
<211> LENGTH: 28
<212> TYPE: DNA
<213> ORGANISM: Chlamydia trachomatis

<400> SEQUENCE: 21
ccgtatgaga aacggatcta agcttgtc                                          28

<210> SEQ ID NO 22
<211> LENGTH: 27
<212> TYPE: DNA
<213> ORGANISM: Chlamydia trachomatis

<400> SEQUENCE: 22
gcgctacaca cgctcaaatc atcgagg                                           27

<210> SEQ ID NO 23
<211> LENGTH: 29
<212> TYPE: DNA
<213> ORGANISM: Chlamydia trachomatis

<400> SEQUENCE: 23
cagcgctaca cacgctcaaa tcatcgagg                                         29

<210> SEQ ID NO 24
<211> LENGTH: 32
<212> TYPE: DNA
<213> ORGANISM: Chlamydia trachomatis

<400> SEQUENCE: 24
cttcagcgct acacacgctc aaatcatcga gg                                     32

<210> SEQ ID NO 25
<211> LENGTH: 24
<212> TYPE: DNA
<213> ORGANISM: Chlamydia trachomatis

<400> SEQUENCE: 25
cgatgatttg agcgtgtgta gcgc                                              24

<210> SEQ ID NO 26
<211> LENGTH: 24
<212> TYPE: DNA
<213> ORGANISM: Chlamydia trachomatis

<400> SEQUENCE: 26
caagagtaca tcggtcaacg aaga                                              24

<210> SEQ ID NO 27
<211> LENGTH: 22
<212> TYPE: DNA
<213> ORGANISM: Chlamydia trachomatis

<400> SEQUENCE: 27
ccccaccatt tttccggagc ga                                                22

<210> SEQ ID NO 28
<211> LENGTH: 25
<212> TYPE: DNA
<213> ORGANISM: Chlamydia trachomatis

<400> SEQUENCE: 28
gggattcctg taacaacaag tcagg                                             25
```

```
<210> SEQ ID NO 29
<211> LENGTH: 27
<212> TYPE: DNA
<213> ORGANISM: Chlamydia trachomatis
<220> FEATURE:
<221> NAME/KEY: misc_feature
<222> LOCATION: (10)..(10)
<223> OTHER INFORMATION: "d" is not C

<400> SEQUENCE: 29
ctgggattcd tgtaacaaca agtcagg                                           27

<210> SEQ ID NO 30
<211> LENGTH: 25
<212> TYPE: DNA
<213> ORGANISM: Chlamydia trachomatis

<400> SEQUENCE: 30
gggattcgtg taacaacaag tcagg                                             25

<210> SEQ ID NO 31
<211> LENGTH: 23
<212> TYPE: DNA
<213> ORGANISM: Chlamydia trachomatis

<400> SEQUENCE: 31
gcttgcacga agtactctag gag                                               23

<210> SEQ ID NO 32
<211> LENGTH: 22
<212> TYPE: DNA
<213> ORGANISM: Chlamydia trachomatis

<400> SEQUENCE: 32
atagcactat agaactctgc aa                                                22

<210> SEQ ID NO 33
<211> LENGTH: 26
<212> TYPE: DNA
<213> ORGANISM: Chlamydia trachomatis

<400> SEQUENCE: 33
catagcacta tagaactctg caagcc                                            26

<210> SEQ ID NO 34
<211> LENGTH: 32
<212> TYPE: DNA
<213> ORGANISM: Chlamydia trachomatis
<220> FEATURE:
<221> NAME/KEY: stem_loop
<222> LOCATION: (1)..(5)
<223> OTHER INFORMATION: non-bacterial, self-complementary so as to
      form a stem of a beacon probe under suitable conditions with
      residues 28-32.
<220> FEATURE:
<221> NAME/KEY: stem_loop
<222> LOCATION: (28)..(32)
<223> OTHER INFORMATION: non-bacterial sequence self-complementary so
      as to form a stem of a beacon probe under suitable conditions
      with residues 1-5.

<400> SEQUENCE: 34
ctggcatagc actatagaac tctgcaagcc ag                                     32

<210> SEQ ID NO 35
```

```
<210> SEQ ID NO 35
<211> LENGTH: 20
<212> TYPE: DNA
<213> ORGANISM: Neisseria gonorrhoeae

<400> SEQUENCE: 35
cgacgtaccg gtttttgttc                                              20

<210> SEQ ID NO 36
<211> LENGTH: 22
<212> TYPE: DNA
<213> ORGANISM: Neisseria gonorrhoeae

<400> SEQUENCE: 36
cggctcctta ttcggtttga cc                                           22

<210> SEQ ID NO 37
<211> LENGTH: 18
<212> TYPE: DNA
<213> ORGANISM: Neisseria gonorrhoeae

<400> SEQUENCE: 37
acaccgcccg gaacccga                                                18

<210> SEQ ID NO 38
<211> LENGTH: 22
<212> TYPE: DNA
<213> ORGANISM: Neisseria gonorrhoeae

<400> SEQUENCE: 38
gaaacaccgc ccggaacccg at                                           22

<210> SEQ ID NO 39
<211> LENGTH: 24
<212> TYPE: DNA
<213> ORGANISM: Neisseria gonorrhoeae
<220> FEATURE:
<221> NAME/KEY: stem_loop
<222> LOCATION: (1)..(5)
<223> OTHER INFORMATION: non-bacterial, self-complementary so as to
      form a stem of a beacon probe under suitable conditions with
      residues 20-24.
<220> FEATURE:
<221> NAME/KEY: stem_loop
<222> LOCATION: (24)..(24)
<223> OTHER INFORMATION: non-bacterial, self-complementary so as to
      form a stem of a beacon probe under suitable conditions with
      residues 1-5.

<400> SEQUENCE: 39
ctcggacacc gcccggaacc cgag                                         24

<210> SEQ ID NO 40
<211> LENGTH: 28
<212> TYPE: DNA
<213> ORGANISM: Chlamydia trachomatis

<400> SEQUENCE: 40
ctacagcaga gttggcagct tcactttc                                     28

<210> SEQ ID NO 41
<211> LENGTH: 22
<212> TYPE: DNA
<213> ORGANISM: Chlamydia trachomatis

<400> SEQUENCE: 41
gtctggcctt tcagcaagtt tc                                           22
```

```
<210> SEQ ID NO 42
<211> LENGTH: 25
<212> TYPE: DNA
<213> ORGANISM: Chlamydia trachomatis

<400> SEQUENCE: 42
aagctgacga gttcatgagg gcagg                                          25

<210> SEQ ID NO 43
<211> LENGTH: 24
<212> TYPE: DNA
<213> ORGANISM: Artificial
<220> FEATURE:
<223> OTHER INFORMATION: synthetic sequence

<400> SEQUENCE: 43
cgatgatttg agcgtgtgta gcgg                                           24

<210> SEQ ID NO 44
<211> LENGTH: 140
<212> TYPE: DNA
<213> ORGANISM: Chlamydia trachomatis

<400> SEQUENCE: 44
caagcttaga tccgtttctc atacggtttt cctcgatgat ttgagcgtgt gtagcgctga    60
agaaaatttg agcaatttca ttttccgctc gtttaatgag tacaatgaaa atccattgcg   120
tagatctccg tttctattgc                                               140
```

PRIMER AND PROBE SEQUENCES FOR DETECTING *CHLAMYDIA TRACHOMATIS*

CROSS-REFERENCE TO RELATED APPLICATION

The present application claims priority to U.S. Provisional Application Ser. No. 60/911,684, filed on Apr. 13, 2007 and is hereby incorporated in its entirety by reference.

FIELD OF THE INVENTION

The invention is directed to compositions and methods for the detection of *Chlamydia trachomatis* plasmids, including a deletion variant recently observed in subjects in Sweden.

BACKGROUND OF THE INVENTION

*Chlamydia trachomatis* (*C. trachomatis* or CT) is a causative agent of common sexually transmitted diseases, including venereal lymphogranuloma, various inflammatory pathologies of the male and female urogenital systems, and trachoma, a chronic disease that affects 500 million people and can lead to blindness. When not timely diagnosed and treated, CT-induced urethritis and cervicitis can led to chronic inflammations, e.g., vaginitis, salpingitis and pelvic inflammation which can result in sterility and extrauterine pregnancy. Furthermore, newborns from infected mothers can contract pulmonary and/or ocular infections during delivery.

The Chlamydiae

Chlamydiae are prokaryotes that exhibit morphologic and structural similarities to Gram negative bacteria including a trilaminar outer membrane that contains lipopolysaccharide and several membrane proteins. Chlamydiae differ from other bacteria by their morphology and a unique developmental cycle. Obligate intracellular parasites, Chlamydiae have a unique biphasic life cycle consisting of a metabolically inactive but infectious extracellular stage and a replicating but non-infectious intracellular stage. The replicative stage of the life-cycle takes place within a membrane-bound inclusion that sequesters the bacteria away from the cytoplasm of the infected host cell.

Many different strains of Chlamydiae have been isolated from mammals (including man) and birds. Strains can be distinguished on the basis of host range, virulence, pathogenesis, and antigenic composition. There is strong DNA sequence identity within each species, but surprisingly little between species, suggesting long-standing evolutionary separation.

A cryptic plasmid (extra-chromosomal DNA) of about 7501 bp and having unknown function is found in almost all CT isolates and is known, for example, in the LGV strain as "pLGV440." The plasmid is not essential for CT survival, but is remarkable in that the sequence is highly conserved across isolates (e.g., see (Comanducci et al., 1990)).

Diagnostic Tests

Rapid and specific diagnostic tests are of utmost importance for successful intervention against CT. Diagnosis based on selective growth of the pathogenic bacteria has been the standard, but cell culturing is time-consuming. Many clinical isolates are difficult to grow in vitro. Because bacterial infection causes antibody production in the host, sera from patients suffering genital tract infections have also been used to diagnose CT infection. However, assays based on serological markers are non-quantitative and often difficult to interpret. For example, antibody titers can be undetectable in acute infections (a false-negative result), persist in uninfected individuals with a past history of infection (a false-positive result), yield a false-positive due to the presence of cross-reacting species (e.g., respiratory infection by different *Chlamydia* species), or not develop at all (a false-negative result) depending on other factors Black et al., 1991; Ngeow, 1996). For these reasons, serology alone is inadequate for the diagnosis of CT infections.

There have been attempts to remedy these inadequacies. For example, the Abbott Laboratories REALTIME™ CT/NG (2G28) and CT (1L31) products use *Chlamydia* cryptic plasmid polymerase chain reaction (PCR) primers and probes in a homogenous real-time format (Pabich et al., 2004). Jalal et al. (Jalal et al., 2006) developed a rotor-gene, real-time PCR assay for detecting, identifying and quantifying CT in a single reaction. Picket et al. (Pickett et al., 2005) were able to determine accurately the copy number of CT and *C. pneumoniae* (N16) also using real-time PCR.

New Challenges in CT Detection

PCR-based methods of CT detection have mined the advantages of the cryptic plasmid found in almost all CT strains. The plasmid is favored as a target for polynucleotide-based diagnosis of CT infection because per bacterium, there are approximately 4-10 copies of the plasmid (Jalal et al., 2006; Palmer and Falkow, 1986; Pickett et al., 2005; Tam et al., 1992).

However, a new variant of CT with a deletion in the plasmid has been detected in Sweden ("CTSW"), following an unexpected 25% decrease in CT infections that was noted in Halland county, Sweden (Ripa and Nilsson, 2006).

For the past decade, laboratories in Sweden have used nucleic acid amplification tests (NAAT) using the cryptic plasmid as the template for DNA amplification to diagnose CT infections.

From mid-September to October 2006, the county microbiology laboratory in Halmstad, Halland county, tested 1700 consecutive incoming specimens with a major outer membrane protein (MOMP)-specific PCR in parallel with Abbott's m2000 plasmid PCR. In 13% of all diagnosed CT cases in Halland county during this period, Ripa et al. found a variant strain that was only positive in MOMP tests. Clinical data indicates no difference from infections with the wild type strains. The strain seems to be spread throughout Sweden, although prevalence in these areas is still unknown.

The part of the plasmid from the variant strain was sequenced. Ripa et al. found a deletion of 377 base pairs in the target area for the CT NAAT tests manufactured by Abbott and Roche (nucleotides 654 to 1030 of Accession No. X06707; SEQ ID NO:4). Twelve variant strains have now been sequenced and found to have the same deletion (Ripa and Nilsson, 2006). Therefore, there exists a need in the art for new NAAT tests that are capable of detecting this variant strain as well as distinguishing this variant strain from other strains of CT.

Publications referred to throughout the specification are herein incorporated by reference in their entireties.

SUMMARY OF THE INVENTION

In a first aspect, the invention is drawn to a combination of polynucleotide reagents useful for amplifying and/or detecting CT and CTSW comprising a first and a second polynucleotide, wherein the first polynucleotide consists essentially of a nucleic acid sequence having at least 70%, 80%, 90%, 95%, or 100% sequence identity with a polynucleotide of SEQ ID NOs:1, 5-9, 11-13 or 14, and complements thereof; and the second polynucleotide consists essentially of a nucleic acid sequence having at least 70%, 80%, 90%, 95%, or 100% sequence identity with a polynucleotide of SEQ ID NOs:2, 10, 15, 16 and 26, and complements thereof. The combination of polynucleotide reagents can further include a third polynucleotide having at least 70%, 80%, 90%, 95%, or 100% sequence identity with a polynucleotide selected from the group consisting of SEQ ID NOs:3, 17-25, 27, 42 and a polynucleotide comprising n nucleotides, wherein 10≤n≤140 consecutive nucleotides of SEQ ID NO:44, and complements thereof.

The invention is also drawn to a second aspect, wherein the combination of polynucleotide reagents of the first aspects further comprise a fourth, fifth and sixth polynucleotides, wherein the combination is useful for detecting and/or amplifying CT and CTSW. In this combination of polynucleotide reagents, the fourth polynucleotide consists essentially of a nucleic acid sequence having at least 70%, 80%, 90%, 95%, or 100% sequence identity with a polynucleotide selected from the group consisting of SEQ ID NOs:28-30 and complements thereof; the fifth polynucleotide consists essentially of a nucleic acid sequence having at least 70%, 80%, 90%, 95%, or 100% sequence identity with a polynucleotide selected from the group consisting of SEQ ID NO:31 and a complement thereof; and the sixth polynucleotide consists essentially of a nucleic acid sequence having at least 70%, 80%, 90%, 95%, or 100% sequence identity with a polynucleotide selected from the group consisting of SEQ ID NOs:32-34 and complements thereof.

The invention is also drawn to a third aspect, wherein the combination of polynucleotide reagents of the first aspect further comprise a fourth, fifth and sixth polynucleotides, wherein the combination is useful for detecting and/or amplifying CT, CTSW and NG. In this combination of polynucleotide reagents, the fourth polynucleotide consists essentially of a nucleic acid sequence having at least 70%, 80%, 90%, 95%, or 100% sequence identity with a polynucleotide of SEQ ID NO:35 and complements thereof; the fifth polynucleotide consists essentially of a nucleic acid sequence having at least 70%, 80%, 90%, 95%, or 100% sequence identity with a polynucleotide of SEQ ID NO:36 and a complement thereof; and the sixth polynucleotide consists essentially of a nucleic acid sequence having at least 70%, 80%, 90%, 95%, or 100% sequence identity with a polynucleotide selected from the group consisting of SEQ ID NOs:37-39 and complements thereof.

The invention is also drawn to a fourth aspect, wherein the combination of polynucleotide reagents of the first aspect further comprise a fourth, fifth, sixth, seventh, eighth and ninth polynucleotides, wherein the combination is useful for detecting and/or amplifying CT, CTSW and NG. In this combination of polynucleotide reagents, the fourth polynucleotide consists essentially of a nucleic acid sequence having at least 70%, 80%, 90%, 95%, or 100% sequence identity with a polynucleotide selected from the group consisting of SEQ ID NOs:28-30 and complements thereof; the fifth polynucleotide consists essentially of a nucleic acid sequence having at least 70%, 80%, 90%, 95%, or 100% sequence identity with a polynucleotide of SEQ ID NO:31 and a complement thereof; the sixth polynucleotide consists essentially of a nucleic acid sequence having at least 70%, 80%, 90%, 95%, or 100% sequence identity with a polynucleotide selected from the group consisting of SEQ ID NOs:32, 33 and 34 and complements thereof; the seventh polynucleotide consists essentially of a nucleic acid sequence having at least 70%, 80%, 90%, 95%, or 100% sequence identity with a polynucleotide of SEQ ID NO:35 or complements thereof; the eighth polynucleotide consists essentially of a nucleic acid sequence having at least 70%, 80%, 90%, 95%, or 100% sequence identity with a polynucleotide of SEQ ID NO:36 or complements thereof; and the ninth polynucleotide consists essentially of a nucleic acid sequence having at least 70%, 80%, 90%, 95%, or 100% sequence identity with a polynucleotide selected from the group consisting of SEQ ID NOs: 37, 38 and 39 and complements thereof.

In each aspect, at least one polynucleotide reagent can include a detectable label or a quencher.

In a fifth aspect, the invention is drawn to kits that include the combination of polynucleotides of aspects 1-5, the kit also including amplification reagents.

In a sixth aspect, the invention is drawn to methods of amplifying and/or detecting CT, CTSW and/or NG, using the combination of polynucleotide reagents of aspects 1-4. These reactions can further include at least one control polynucleotide, positive and/or negative, as well as for those that can be used for normalization. However, when detecting CT or CTSW, if the reaction consists of 7.5 units of a DNA polymerase, 15 mM Tris-HCl, pH 8.0, 50 mM KCl, 9.5 mM $MgCl_2$, 0.2 mM dNTPs, 500 nM of the first and second polynucleotides and 60 nM ROX then if the first polynucleotide consists of a nucleic acid sequence of SEQ ID NO:1 or a complement thereof, then the second polynucleotide does not consist of a nucleic acid sequence of SEQ ID NO:16 or a complement thereof, and the third polynucleotide does not consist of a nucleic acid sequence of SEQ ID NO:23 or complement thereof;

if the first polynucleotide consists of a nucleic acid sequence of SEQ ID NO:1 or a complement thereof, then the second polynucleotide does not consist of a nucleic acid sequence of SEQ ID NO:2 or a complement thereof, and the third polynucleotide does not consist of a nucleic acid sequence of SEQ ID NO:22 or a complement thereof if the first polynucleotide consists of a nucleic acid sequence of SEQ ID NO:8 or 9 or complements thereof, then the second polynucleotide does not consist of a nucleic acid sequence SEQ ID NOs:10 or 26 or complements thereof, and the third polynucleotide does not consist of a nucleic acid sequence of SEQ ID NO:17 or a complement thereof;

if the first polynucleotide consists of a nucleic acid sequence of SEQ ID NO:5 or 6 or complements thereof, then the second polynucleotide does not consist of a nucleic acid sequence of SEQ ID NO:10 or a complement thereof, and the third polynucleotide does not consist of a nucleic acid sequence of SEQ ID NO:19 or a complement thereof; and if the first polynucleotide consists of a nucleic acid sequence of SEQ ID NO:14 or a complement thereof, then the second polynucleotide does not consist of a nucleic acid sequence of SEQ ID NO:2 or a complement thereof, and the third polynucleotide does not consist of a nucleic acid sequence of SEQ ID NO:22 or complement thereof

DETAILED DESCRIPTION

The present invention solves the problems of both detecting the CTSW strain, as well as distinguishing the CTSW from other CT strains under certain assay conditions. By providing probes and primers that have been carefully designed and rigorously tested, the diagnosis of CT infection, whether infection is by CT or CTSW is now straightforward and certain.

The present invention specifically combines polynucleotide sequences that when used together, produce sensitive, specific and reproducible detection of both CT and CTSW strains. Not only can CTSW be identified, but samples can be simultaneously determined if they contain either CT, CTSW or both.

Moreover, the invention also provides for methods, assays and kits for detecting CT and CTSW sequences.

The inventors obtained and analyzed DNA preparations from 38 clinical specimens from three counties in Sweden. The various sample types included urine, urine combined with cervical swabs, urethral swabs, and ocular swabs. A region of approximately 1,000 nucleotides within the cryptic plasmid was amplified in vitro, and the resulting amplified region analyzed for size. All 38 samples showed a similar deletion of approximately 350 to 400 base pairs (bp). Thirty-six samples were then sequenced. An identical 377 bp deletion was found in all 36 samples.

The inventors then evaluated multiple combinations of primers and probes for detection of this deletion strain by targeting regions outside of the deletion region. One selected primer-probe set was shown to detect *Chlamydia trachomatis* containing the wild type cryptic plasmid as well as the deletion variant. This primer-probe set also detected all fourteen members of a panel of *Chlamydia trachomatis* serovars (a serovar differs from other serovars by the proteins found on the bacterium's cell surface).

The molecular "tools" of the invention include the sequences shown in Table 1, and their complements.

Table 1

Primer and probe sequences

| SEQ ID NO: | Primer name | Sequence | Bases |
|---|---|---|---|
| 1 | CP 2512_2537 (forward) | caagcttaga tccgtttctc atacgg | 26 |
| 2 | CP 2624_2651 (reverse) | gcaatagaaa cggagatcta cgcaatgg | 28 |
| 3 | CP 2542_2568 probe (forward) | cctcgatgat ttgagcgtgt gtagcgc | 27 |
| 5 | CP 1223_1249 (forward) | ccttcattat gtcggagtct gagcacc | 27 |
| 6 | CP 1224_1249 (forward) | cttcattatg tcggagtctg agcacc | 26 |
| 7 | CP 1233_1256 (forward) | gtcggagtct gagcaccta ggcg | 24 |
| 8 | CP 1269_1295 (forward) | cacagcggtt gctcgaagca cgtgcgg | 27 |
| 9 | CP 1272_1295 (forward) | agcggttgct cgaagcacgt gcgg | 24 |
| 10 | CP 1399_1424 (reverse) | caagagtaca tcggtcaacg aagagg | 26 |
| 11 | CP 2424_2448 (forward) | cggcttggga agagcttttg cggcg | 25 |
| 12 | CP 2430_2448 (forward) | gggaagagct tttgcggcg | 19 |
| 13 | CP 2472_2498 (forward) | cgtatctcgg gttaatgttg catgatg | 27 |
| 14 | CP 2472_2495 (forward) | cgtatctcgg gttaatgttg catg | 24 |
| 15 | CP 2596_2618 (reverse) | cattgtactc attaaacgag cgg | 23 |
| 16 | CP 2650_2677 (reverse) | gtcaagcctt ccctttatac gctcaagc | 28 |
| 17 | CP 1341_1368 probe (reverse) | ggtggggtta aggcaaatcg cccgcacg | 28 |
| 18 | CP 1355_1384 probe (forward) | gccttaaccc caccattttt ccggagcgag | 30 |
| 19 | CP 1362_1389 probe (forward) | ccccaccatt tttccggagc gagttacg | 28 |
| 20 | CP 2510_2537 probe (forward) | gacaagctta gatccgtttc tcatacgg | 28 |

Primer and probe sequences

| SEQ ID NO: | Primer name | Sequence | Bases |
|---|---|---|---|
| 21 | CP 2510_2537 probe (reverse) | ccgtatgaga aacggatcta agcttgtc | 28 |
| 22 | CP 2542_2568 probe (reverse) | gcgctacaca cgctcaaatc atcgagg | 27 |
| 23 | CP 2542_2570 probe (reverse) | cagcgctaca cacgctcaaa tcatcgagg | 29 |
| 24 | CP 2542_2573 probe (reverse) | cttcagcgct acacacgctc aaatcatcga gg | 32 |
| 25 | CP 2545_2568 probe (forward) | cgatgatttg agcgtgtgta gcgc | 24 |

The following terms are used to describe the invention.

Definitions

"Specifically hybridize" refers to the ability of a nucleic acid to bind detectably and specifically to a second nucleic acid. Polynucleotides specifically hybridize with target nucleic acid strands under hybridization and wash conditions that minimize appreciable amounts of detectable binding by non-specific nucleic acids.

"Target sequence" or "target nucleic acid sequence" means a nucleic acid sequence of CT or CTSW or complements thereof, that is amplified, detected, or both using one or more of the polynucleotides herein provided. Additionally, while the term target sequence sometimes refers to a double stranded nucleic acid sequence, a target sequence can also be single-stranded. In cases where the target is double-stranded, polynucleotide primer sequences of the present invention preferably amplify both strands of the target sequence. A target sequence can be selected that is more or less specific for a particular organism. For example, the target sequence can be specific to an entire genus, to more than one genus, to a species or subspecies, serogroup, auxotype, serotype, strain, isolate or other subset of organisms.

"Test sample" means a sample taken from an organism or biological fluid that can contain a CT or CTSW target sequence. A test sample can be taken from any source, for example, tissue, blood, saliva, sputa, mucus, sweat, urine, urethral swabs, cervical swabs, urogenital or anal swabs, conjunctival swabs, ocular lens fluid, cerebral spinal fluid, etc. A test sample can be used (i) directly as obtained from the source; or (ii) following a pre-treatment to modify the character of the sample. Thus, a test sample can be pre-treated prior to use by, for example, preparing plasma or serum from blood, disrupting cells or viral particles, preparing liquids from solid materials, diluting viscous fluids, filtering liquids, adding reagents, purifying nucleic acids, etc.

"Label" means a molecule or moiety having a property or characteristic that is capable of detection and, optionally, of quantitation. A label can be directly detectable, as with, for example, radioisotopes, fluorophores, chemiluminophores, enzymes, colloidal particles, fluorescent microparticles; or a label can be indirectly detectable, as with, for example, specific binding members. Directly detectable labels sometimes require additional components, such as substrates, triggering reagents, quenching moieties, and light to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known and include, for example, any chemical means and/or physical means that does not destroy the specific binding property of the specific binding member or the detectable property of the label. "Specific binding member" means a member of a binding pair, i.e., two different molecules where one of the molecules through, for example, chemical or physical means, specifically binds to the other molecule. In addition to antigen and antibody specific binding pairs, other examples of specific binding pairs include (strept)avidin and biotin; haptens and antibodies specific for haptens; complementary nucleotide sequences; enzyme cofactors or substrates and enzymes; etc.

"Quantum dot" (QD) means a nano-scale semiconductor crystalline structure, usually made from cadmium selenide, and absorbs light and then re-emits it a couple of nanoseconds later in a specific color.

QDs are commercially available (e.g., Invitrogen Corp.; Carlsbad, Calif.) with a variety of conjugated or reactive surfaces, e.g., amino, carboxyl, streptavidin, protein A, biotin, and immunoglobulins.

A "polynucleotide" is a nucleic acid polymer of ribonucleic acid (RNA), deoxyribonucleic acid (DNA), modified RNA or DNA, or RNA or DNA mimetics (such as, PNAs), and derivatives thereof, and homologues thereof. Thus, polynucleotides include polymers composed of naturally occurring nucleobases, sugars and covalent inter-nucleoside (backbone) linkages as well as polymers having non-naturally-occurring portions that function similarly. Such modified or substituted nucleic acid polymers are well known in the art and for the purposes of the present invention, are referred to as "analogues." Oligonucleotides are generally short polynucleotides from about 10 to up to about 160 or 200 nucleotides.

"CT or CTSW variant polynucleotide" or "CT or CTSW variant nucleic acid sequence" means a CT or CTSW variant polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence of CT or CTSW. Variants do not encompass the native nucleotide sequence.

Ordinarily, CT or CTSW variant polynucleotides are at least about 8 nucleotides in length, often at least about 9, 10, 11, 12, 13, 14, 15, 16, 17, 18, 19, 20, 21, 22, 23, 24, 25, 26, 27, 28, 29 30, 35, 40, 45, 50, 55, 60 nucleotides in length, or even about 75-200 nucleotides in length, or more.

"Percent (%) nucleic acid sequence identity" with respect to CT or CTSW-nucleic acid sequences is defined as the percentage of nucleotides in a candidate sequence that are identical with the nucleotides in the CT or CTSW sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

$$\text{\% nucleic acid sequence identity} = W/Z \cdot 100$$

where

W is the number of nucleotides cored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

"Consisting essentially of a polynucleotide having a % sequence identity" means, when applied to a polynucleotide, that the polynucleotide does not substantially differ in length, but in sequence. Thus, a polynucleotide "A" consisting essentially of a polynucleotide having 80% sequence identity to a known sequence "B" of 100 nucleotides means that polynucleotide "A" is about 100 nts long, but up to 20 nts can vary from the "B" sequence. The polynucleotide can be longer or shorter due to the addition of 1-15 nucleotides on the termini to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of."

Orthologs (i.e., nucleic acids encoding CT or CTSW derived from species other than human) or other related sequences (e.g., paralogs and xenologs) can be obtained by low, moderate or high stringency hybridization with all or a portion of the particular human sequence as a probe using methods well known in the art for nucleic acid hybridization and cloning.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favor specific hybridizations (high stringency), which can be used to identify, for example, full-length clones from a library. Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide, which decreases DNA duplex stability. A common approach is to vary the temperature: higher relative temperatures result in more stringent reaction conditions. (Ausubel et al., 1987) provide an excellent explanation of stringency of hybridization reactions.

To hybridize under "stringent conditions" describes hybridization protocols in which nucleotide sequences at least 60% homologous to each other remain hybridized.

Polynucleotides can include other appended groups such as peptides (e.g., for targeting host cell receptors in vivo), or agents facilitating transport across the cell membrane. In addition, oligonucleotides can be modified with hybridization-triggered cleavage agents (van der Krol et al., 1988) or intercalating agents (Zon, 1988). The oligonucleotide can be conjugated to another molecule, e.g., a peptide, a hybridization triggered cross-linking agent, a transport agent, a hybridization-triggered cleavage agent, and the like.

Useful polynucleotide analogues include polymers having modified backbones or non-natural inter-nucleoside linkages. Modified backbones include those retaining a phosphorus atom in the backbone, such as phosphorothioates, chiral phosphorothioates, phosphorodithioates, phosphotriesters, aminoalkylphosphotriesters, methyl and other alkyl phosphonates, as well as those no longer having a phosphorus atom, such as backbones formed by short chain alkyl or cycloalkyl inter-nucleoside linkages, mixed heteroatom and alkyl or cycloalkyl inter-nucleoside linkages, or one or more short chain heteroatomic or heterocyclic inter-nucleoside linkages. Modified nucleic acid polymers (analogues) can contain one or more modified sugar moieties.

Analogs that are RNA or DNA mimetics, in which both the sugar and the inter-nucleoside linkage of the nucleotide units are replaced with novel groups, are also useful. In these mimetics, the base units are maintained for hybridization with the target sequence. An example of such a mimetic, which has been shown to have excellent hybridization properties, is a peptide nucleic acid (PNA) (Buchardt et al., 1992; Nielsen et al., 1991).

The realm of nucleotides includes derivatives wherein the nucleic acid molecule has been covalently modified by substitution, chemical, enzymatic, or other appropriate means with a moiety other than a naturally occurring nucleotide, for example with a moiety that functions as a label, as described herein.

The polynucleotides of the present invention thus comprise primers and probes that specifically hybridize to target sequences, for example the nucleic acid molecules having any one of the nucleic acid sequences of SEQ ID NOs:1-3 and 5-25, including analogues and/or derivatives of the nucleic acid sequences, and homologs thereof. The polynucleotides of the invention can be used as primers and/or probes to amplify or detect Chlamydia trachomatis, including CTSW.

The polynucleotides of SEQ ID NOs:1-3 and 5-25 can be prepared by conventional techniques, such as solid-phase synthesis using commercially available equipment, such as that available from Applied Biosystems USA Inc. (Foster City, Calif.; USA), DuPont, (Wilmington, Del.; USA), or Milligen (Bedford, Mass.; USA). Modified polynucleotides, such as phosphorothioates and alkylated derivatives, can also be readily prepared by similar methods known in the art (Fino, 1995; Mattingly, 1995; Ruth, 1990).

The polynucleotides according to the present invention can be used as probes for the detection, or quantitation, or both, of CT or CTSW nucleic acids in a test sample. The test sample is contacted with at least one of the polynucleotides of SEQ ID NOs:1-3 and 5-25 under suitable hybridization conditions and the hybridization between the target sequence and at least one of the polynucleotides is then detected by methods well-known in the art.

"Probes" are polynucleotide sequences of variable length, preferably at least about 10 nt, 100 nt, or more depending on the specific use. Probes are used to detect identical, similar, or complementary polynucleotide sequences. Longer length probes can be obtained from a natural or recombinant source, highly specific, and much slower to hybridize than shorter-length oligomer probes. Probes can be single-, double-, or more-stranded and designed to have specificity in PCR, membrane-based hybridization technologies, or enzyme-linked immunoadsorbent assay (ELISA)-like technologies. Probes can be substantially purified oligonucleotides that hybridize under stringent conditions to 12, 25, 50, 100, 150, 200, 250, 300, 350 or 400 base polynucleotides; such as an mRNA target.

Detectable labels can be incorporated into the polynucleotides of SEQ ID NOs:1-3 and 5-25 such that the ability of the polynucleotide to hybridize with its target sequence is not adversely affected.

"Capture labels" are typically used to distinguish extension products, and probes associated with any such products, from other amplification reactants. Specific binding members are well suited for this purpose. Such probes can be blocked at their 3' ends so that they are not extended under hybridization conditions. Methods for preventing extension of a probe are well known and are a matter of choice for one skilled in the art. Typically, adding a phosphate group to the 3' end of the probe suffices to block probe extension.

In cases where labels are used to detect primer-amplified products, primer sequences optionally can be labeled with either a capture label or a detectable label. The probe sequence is used to hybridize with the sequence generated by the primer sequence, and typically hybridizes with a sequence that does not include the primer sequence. The probe sequence can also be labeled with either a capture label or a detection label with the caveat that when the primer is labeled with a capture label, the probe is labeled with a detection label, and ice versa. Upon formation of the copy sequence: probe hybrids, the differential labels (i.e., capture and detection labels) on the copy sequence and probe sequence can be used to separate and detect such hybrids. In one embodiment of the present invention, detection is performed according to the protocols used by the commercially available Abbott m2000™ instrumentation (Abbott Molecular Inc., Des Plaines, Ill.; USA).

SEQ ID NOs:1-3 and 5-25 can also be used as capture probes or disclosure probes in sandwich-type assays. Briefly, the polynucleotide capture probe is attached to a solid support and brought into contact with a test sample under suitable hybridization conditions such that a probe:target hybrid is formed between the capture probe and any target nucleic acid present in the test sample. After one or more appropriate washing steps, the probe:target hybrid is detected, usually by a second "disclosure" probe or a specific antibody that recognizes the hybrid molecule.

The polynucleotides of the invention can be used in modified nucleic acid hybridization assays. For example, Pandian et al. (Pandian et al., 1997) disclose a method to amplify the detection signal in a nucleic acid hybridization assay. A first polynucleotide probe sequence is hybridized to a target sequence, the probe:target hybrid is subsequently immuno-captured and immobilized. A second polynucleotide probe that contains many repeating sequence units is then hybridized to the probe component of the probe:target hybrid. The complex is detected by hybridizing using labeled nucleic acid sequence probes, one to each of the repeating sequence units in the second probe. The attachment of multiple labeled probes to the second probe amplifies the detection signal and increases assay sensitivity. SEQ ID NOs:1-3 and 5-25 can be used in such modified hybridization assays, either directly as first probes, or as second probes that have been modified to incorporate additional repeating sequence units.

Practicing the Invention

Amplification and Detection of CT and CTSW Nucleotide Sequences

The polynucleotides of SEQ ID NOs:1-3 and 5-25 can be used as primer/probe sets to amplify and detect CT or CTSW in a sample. The primers in any particular primer/probe set (sets are exemplified in Table 2) can be used to amplify a target sequence. In most cases, the probe hybridizes to the copies of the target sequence generated by one of the primers and generally facilitates detecting any copies of the target sequence generated during the course of the amplification reaction. All of the primer/probe sets can be used according to nucleic acid amplification procedures to specifically and sensitively detect either CT or CTSW, or both CT and CTSW when the appropriate primers and probes are combined. The individual primers and probes of the primer/probe sets can also be used in combination with other primers and/or probes.

Amplification procedures are well-known in the art and include the polymerase chain reaction (PCR), TMA, rolling circle amplification, nucleic acid sequence based amplification (NASBA), ligase chain reaction and strand displacement amplification (SDA). One skilled in the art will understand that for use in certain amplification techniques the primers may need to be modified; for example, SDA primers usually comprise additional nucleotides near the 5' ends that constitute a recognition site for a restriction endonuclease. For NASBA, the primers include additional nucleotides near the 5' end that constitute an RNA polymerase promoter. Polynucleotides thus modified are considered to be within the scope of the present invention.

Criteria need to be considered when selecting primers for amplification reactions. For example, the primers should be selected such that the likelihood of forming 3' duplexes is minimized, and such that the melting temperatures ($T_m$) are sufficiently similar to optimize annealing to the target sequence and minimize non-specific annealing. In this context, the polynucleotides according to the present invention are provided in combinations that can be used as primers in amplification reactions to specifically amplify target nucleic acid sequences. These combinations are provided in Table 2; those sequences that can be used as probes are elaborated below.

TABLE 2

Exemplary combinations of primers and probes for detecting CT and CTSW

| Combination | Forward Primer | Reverse Primer | Probe |
|---|---|---|---|
| 1 | SEQ ID NO:5 (CP 1223_1249 Forward) | SEQ ID NO:10 (CP 1399_1424 Reverse) | SEQ ID NO:17 (CP 1341_1368 (Reverse)) |
| 2 | SEQ ID NO:6 (CP 1224_1249 Forward) | SEQ ID NO:10 (CP 1399_1424 Reverse) | SEQ ID NO:17 (CP 1341_1368 (Reverse)) |
| 3 | SEQ ID NO:7 (CP 1233_1256 Forward) | SEQ ID NO:10 (CP 1399_1424 Reverse) | SEQ ID NO:17 (CP 1341_1368 (Reverse)) |
| 4 | SEQ ID NO:8 (CP 1269_1295 Forward) | SEQ ID NO:10 (CP 1399_1424 Reverse) | SEQ ID NO:17 (CP 1341_1368 (Reverse)) |
| 5 | SEQ ID NO:9 (CP 1272_1295 Forward) | SEQ ID NO:10 (CP 1399_1424 Reverse) | SEQ ID NO:17 (CP 1341_1368 (Reverse)) |
| 6 | SEQ ID NO:5 (CP 1223_1249 Forward) | SEQ ID NO:10 (CP 1399_1424 Reverse) | SEQ ID NO:18 (CP 1355_1384 (Forward)) |
| 7 | SEQ ID NO:6 (CP 1224_1249 Forward) | SEQ ID NO:10 (CP 1399_1424 Reverse) | SEQ ID NO:18 (CP 1355_1384 (Forward)) |
| 8 | SEQ ID NO:7 (CP 1233_1256 Forward) | SEQ ID NO:10 (CP 1399_1424 Reverse) | SEQ ID NO:18 (CP 1355_1384 (Forward)) |
| 9 | SEQ ID NO:8 (CP 1269_1295 Forward) | SEQ ID NO:10 (CP 1399_1424 Reverse) | SEQ ID NO:18 (CP 1355_1384 (Forward)) |
| 10 | SEQ ID NO:9 (CP 1272_1295 Forward) | SEQ ID NO:10 (CP 1399_1424 Reverse) | SEQ ID NO:18 (CP 1355_1384 (Forward)) |
| 11 | SEQ ID NO:5 (CP 1223_1249 Forward) | SEQ ID NO:10 (CP 1399_1424 Reverse) | SEQ ID NO:19 (SEQ ID NO:19 (CP 1362_1389 (Forward))) |
| 12 | SEQ ID NO:6 (CP 1224_1249 Forward) | SEQ ID NO:10 (CP 1399_1424 Reverse) | SEQ ID NO:19 (SEQ ID NO:19 (CP 1362_1389 (Forward))) |
| 13 | SEQ ID NO:7 (CP 1233_1256 Forward) | SEQ ID NO:10 (CP 1399_1424 Reverse) | SEQ ID NO:19 (SEQ ID NO:19 (CP 13621389 (Forward))) |
| 14 | SEQ ID NO:8 (CP 1269_1295 Forward) | SEQ ID NO:10 (CP 1399_1424 Reverse) | SEQ ID NO:19 (SEQ ID NO:19 (CP 1362_1389 (Forward))) |
| 15 | SEQ ID NO:9 (CP 1272_1295 Forward) | SEQ ID NO:10 (CP 1399_1424 Reverse) | SEQ ID NO:19 (SEQ ID NO:19 (CP 1362_1389 (Forward))) |
| 16 | SEQ ID NO:5 (CP 1223_1249 Forward) | SEQ ID NO:26[1] | SEQ ID NO:17 (CP 1341_1368 (Reverse)) |
| 17 | SEQ ID NO:6 (CP 1224_1249 Forward) | SEQ ID NO:26[1] | SEQ ID NO:17 (CP 1341_1368 (Reverse)) |
| 18 | SEQ ID NO:7 (CP 1233_1256 Forward) | SEQ ID NO:26[1] | SEQ ID NO:17 (CP 1341_1368 (Reverse)) |
| 19 | SEQ ID NO:8 (CP 1269_1295 Forward) | SEQ ID NO:26[1] | SEQ ID NO:17 (CP 1341_1368 (Reverse)) |
| 20 | SEQ ID NO:9 (CP 1272_1295 Forward) | SEQ ID NO:26[1] | SEQ ID NO:17 (CP 1341_1368 (Reverse)) |
| 21 | SEQ ID NO:5 (CP 1223_1249 Forward) | SEQ ID NO:26[1] | SEQ ID NO:18 (CP 1355_1384 (Forward)) |
| 22 | SEQ ID NO:6 (CP 1224_1249 Forward) | SEQ ID NO:26[1] | SEQ ID NO:18 (CP 1355_1384 (Forward)) |
| 23 | SEQ ID NO:7 (CP 1233_1256 Forward) | SEQ ID NO:26[1] | SEQ ID NO:18 (CP 1355_1384 (Forward)) |
| 24 | SEQ ID NO:8 (CP 1269_1295 Forward) | SEQ ID NO:26[1] | SEQ ID NO:18 (CP 1355_1384 (Forward)) |
| 25 | SEQ ID NO:9 (CP 1272_1295 Forward) | SEQ ID NO:26[1] | SEQ ID NO:18 (CP 1355_1384 (Forward)) |

TABLE 2-continued

Exemplary combinations of primers and probes for detecting CT and CTSW

| Combination | Forward Primer | Reverse Primer | Probe |
|---|---|---|---|
| 26 | SEQ ID NO:5 (CP 1223_1249 Forward) | SEQ ID NO:26[1] (CP 1362_1389 (Forward)) | SEQ ID NO:19 |
| 27 | SEQ ID NO:6 (CP 1224_1249 Forward) | SEQ ID NO:26[1] (CP 1362_1389 (Forward)) | SEQ ID NO:19 |
| 28 | SEQ ID NO:7 (CP 1233_1256 Forward) | SEQ ID NO:26[1] (CP 1362_1389 (Forward)) | SEQ ID NO:19 |
| 29 | SEQ ID NO:8 (CP 1269_1295 Forward) | SEQ ID NO:26[1] (CP 1362_1389 (Forward)) | SEQ ID NO:19 |
| 30 | SEQ ID NO:9 (CP 1272_1295 Forward) | SEQ ID NO:26[1] (CP 1362_1389 (Forward)) | SEQ ID NO:19 |
| 31 | SEQ ID NO:11 (CP 2424_2448 Forward) | SEQ ID NO:2 (CP 2624_2651 Reverse) | SEQ ID NO:21 (CP 2510_2537 (Reverse)) |
| 32 | SEQ ID NO:12 (CP 2430_2448 Forward) | SEQ ID NO:2 (CP 2624_2651 Reverse) | SEQ ID NO:21 (CP 2510_2537 (Reverse)) |
| 33 | SEQ ID NO:13 (CP 2472_2498 Forward) | SEQ ID NO:2 (CP 2624_2651 Reverse) | SEQ ID NO:21 (CP 2510_2537 (Reverse)) |
| 34 | SEQ ID NO:14 (CP 2472_2495 Forward) | SEQ ID NO:2 (CP 2624_2651 Reverse) | SEQ ID NO:21 (CP 2510_2537 (Reverse)) |
| 35 | SEQ ID NO:11 (CP 2424_2448 Forward) | SEQ ID NO:2 (CP 2624_2651 Reverse) | SEQ ID NO:21 (CP 2510_2537 (Forward)) |
| 36 | SEQ ID NO:12 (CP 2430_2448 Forward) | SEQ ID NO:2 (CP 2624_2651 Reverse) | SEQ ID NO:21 (CP 2510_2537 (Forward)) |
| 37 | SEQ ID NO:13 (CP 2472_2498 Forward) | SEQ ID NO:2 (CP 2624_2651 Reverse) | SEQ ID NO:21 (CP 2510_2537 (Forward)) |
| 38 | SEQ ID NO:14 (CP 2472_2495 Forward) | SEQ ID NO:2 (CP 2624_2651 Reverse) | SEQ ID NO:21 (CP 2510_2537 (Forward)) |
| 39 | SEQ ID NO:11 (CP 2424_2448 Forward) | SEQ ID NO:2 (CP 2624_2651 Reverse) | SEQ ID NO:3 (CP2542_2568 (Forward)) |
| 40 | SEQ ID NO:12 (CP 2430_2448 Forward) | SEQ ID NO:2 (CP 2624_2651 Reverse) | SEQ ID NO:3 (CP2542_2568 (Forward)) |
| 41 | SEQ ID NO:13 (CP 2472_2498 Forward) | SEQ ID NO:2 (CP 2624_2651 Reverse) | SEQ ID NO:3 (CP2542_2568 (Forward)) |
| 42 | SEQ ID NO:14 (CP 2472_2495 Forward) | SEQ ID NO:2 (CP 2624_2651 Reverse) | SEQ ID NO:3 (CP2542_2568 (Forward)) |
| 43 | SEQ ID NO:1 (CP 2512_2537 Forward) | SEQ ID NO:2 (CP 2624_2651 Reverse) | SEQ ID NO:3 (CP2542_2568 (Forward)) |
| 44 | SEQ ID NO:11 (CP 2424_2448 Forward) | SEQ ID NO:2 (CP 2624_2651 Reverse) | SEQ ID NO:22 (CP 2542_2568 (Reverse)) |
| 45 | SEQ ID NO:12 (CP 2430_2448 Forward) | SEQ ID NO:2 (CP 2624_2651 Reverse) | SEQ ID NO:22 (CP 2542_2568 (Reverse)) |
| 46 | SEQ ID NO:13 (CP 2472_2498 Forward) | SEQ ID NO:2 (CP 2624_2651 Reverse) | SEQ ID NO:22 (CP 2542_2568 (Reverse)) |
| 47 | SEQ ID NO:14 (CP 2472_2495 Forward) | SEQ ID NO:2 (CP 2624_2651 Reverse) | SEQ ID NO:22 (CP 2542_2568 (Reverse)) |
| 48 | SEQ ID NO:1 (CP 2512_2537 Forward) | SEQ ID NO:2 (CP 2624_2651 Reverse) | SEQ ID NO:22 (CP 2542_2568 (Reverse)) |
| 49 | SEQ ID NO:11 (CP 2424_2448 Forward) | SEQ ID NO:2 (CP 2624_2651 Reverse) | SEQ ID NO:23 (CP 2542_2570 (Reverse)) |
| 50 | SEQ ID NO:12 (CP 2430_2448 Forward) | SEQ ID NO:2 (CP 2624_2651 Reverse) | SEQ ID NO:23 (CP 2542_2570 (Reverse)) |
| 51 | SEQ ID NO:13 (CP 2472_2498 Forward) | SEQ ID NO:2 (CP 2624_2651 Reverse) | SEQ ID NO:23 (CP 2542_2570 (Reverse)) |
| 52 | SEQ ID NO:14 (CP 2472_2495 Forward) | SEQ ID NO:2 (CP 2624_2651 Reverse) | SEQ ID NO:23 (CP 2542_2570 (Reverse)) |
| 53 | SEQ ID NO:1 (CP 2512_2537 Forward) | SEQ ID NO:2 (CP 2624_2651 Reverse) | SEQ ID NO:23 (CP 2542_2570 (Reverse)) |
| 54 | SEQ ID NO:11 (CP 2424_2448 Forward) | SEQ ID NO:2 (CP 2624_2651 Reverse) | SEQ ID NO:24 (CP 2542_2573 (Reverse)) |
| 55 | SEQ ID NO:12 (CP 2430_2448 Forward) | SEQ ID NO:2 (CP 2624_2651 Reverse) | SEQ ID NO:24 (CP 2542_2573 (Reverse)) |
| 56 | SEQ ID NO:13 (CP 2472_2498 Forward) | SEQ ID NO:2 (CP 2624_2651 Reverse) | SEQ ID NO:24 (CP 2542_2573 (Reverse)) |
| 57 | SEQ ID NO:14 (CP 2472_2495 Forward) | SEQ ID NO:2 (CP 2624_2651 Reverse) | SEQ ID NO:24 (CP 2542_2573 (Reverse)) |
| 58 | SEQ ID NO:1 (CP 2512_2537 Forward) | SEQ ID NO:2 (CP 2624_2651 Reverse) | SEQ ID NO:24 (CP 2542_2573 (Reverse)) |
| 59 | SEQ ID NO:11 (CP 2424_2448 Forward) | SEQ ID NO:2 (CP 2624_2651 Reverse) | SEQ ID NO:25 (CP 2545_2568 (Forward)) |
| 60 | SEQ ID NO:12 (CP 2430_2448 Forward) | SEQ ID NO:2 (CP 2624_2651 Reverse) | SEQ ID NO:25 (CP 2545_2568 (Forward)) |
| 61 | SEQ ID NO:13 (CP 2472_2498 Forward) | SEQ ID NO:2 (CP 2624_2651 Reverse) | SEQ ID NO:25 (CP 2545_2568 (Forward)) |
| 62 | SEQ ID NO:14 (CP 2472_2495 Forward) | SEQ ID NO:2 (CP 2624_2651 Reverse) | SEQ ID NO:25 (CP 2545_2568 (Forward)) |
| 63 | SEQ ID NO:1 (CP 2512_2537 Forward) | SEQ ID NO:2 (CP 2624_2651 Reverse) | SEQ ID NO:25 (CP 2545_2568 (Forward)) |

TABLE 2-continued

Exemplary combinations of primers and probes for detecting CT and CTSW

| Combination | Forward Primer | Reverse Primer | Probe |
|---|---|---|---|
| 64 | SEQ ID NO:11 (CP 2424_2448 Forward) | SEQ ID NO:2 (CP 2624_2651 Reverse) | SEQ ID NO:43[3] |
| 65 | SEQ ID NO:12 (CP 2430_2448 Forward) | SEQ ID NO:2 (CP 2624_2651 Reverse) | SEQ ID NO:43[3] |
| 66 | SEQ ID NO:13 (CP 2472_2498 Forward) | SEQ ID NO:2 (CP 2624_2651 Reverse) | SEQ ID NO:43[3] |
| 67 | SEQ ID NO:14 (CP 2472_2495 Forward) | SEQ ID NO:2 (CP 2624_2651 Reverse) | SEQ ID NO:43[3] |
| 68 | SEQ ID NO:1 (CP 2512_2537 Forward) | SEQ ID NO:2 (CP 2624_2651 Reverse) | SEQ ID NO:43[3] |
| 69 | SEQ ID NO:11 (CP 2424_2448 Forward) | SEQ ID NO:16 (CP 2650_2677 Reverse) | SEQ ID NO:21 (CP 2510_2537 (Reverse)) |
| 70 | SEQ ID NO:12 (CP 2430_2448 Forward) | SEQ ID NO:16 (CP 2650_2677 Reverse) | SEQ ID NO:21 (CP 2510_2537 (Reverse)) |
| 71 | SEQ ID NO:13 (CP 2472_2498 Forward) | SEQ ID NO:16 (CP 2650_2677 Reverse) | SEQ ID NO:21 (CP 2510_2537 (Reverse)) |
| 72 | SEQ ID NO:14 (CP 2472_2495 Forward) | SEQ ID NO:16 (CP 2650_2677 Reverse) | SEQ ID NO:21 (CP 2510_2537 (Reverse)) |
| 73 | SEQ ID NO:11 (CP 2424_2448 Forward) | SEQ ID NO:16 (CP 2650_2677 Reverse) | SEQ ID NO:20 (CP 2510_2537 (Forward)) |
| 74 | SEQ ID NO:12 (CP 2430_2448 Forward) | SEQ ID NO:16 (CP 2650_2677 Reverse) | SEQ ID NO:20 (CP 2510_2537 (Forward)) |
| 75 | SEQ ID NO:13 (CP 2472_2498 Forward) | SEQ ID NO:16 (CP 2650_2677 Reverse) | SEQ ID NO:20 (CP 2510_2537 (Forward)) |
| 76 | SEQ ID NO:14 (CP 2472_2495 Forward) | SEQ ID NO:16 (CP 2650_2677 Reverse) | SEQ ID NO:20 (CP 2510_2537 (Forward)) |
| 77 | SEQ ID NO:11 (CP 2424_2448 Forward) | SEQ ID NO:16 (CP 2650_2677 Reverse) | SEQ ID NO:3 (CP 2542_2568 (Forward)) |
| 78 | SEQ ID NO:12 (CP 2430_2448 Forward) | SEQ ID NO:16 (CP 2650_2677 Reverse) | SEQ ID NO:3 (CP 2542_2568 (Forward)) |
| 79 | SEQ ID NO:13 (CP 2472_2498 Forward) | SEQ ID NO:16 (CP 2650_2677 Reverse) | SEQ ID NO:3 (CP 2542_2568 (Forward)) |
| 80 | SEQ ID NO:14 (CP 2472_2495 Forward) | SEQ ID NO:16 (CP 2650_2677 Reverse) | SEQ ID NO:3 (CP 2542_2568 (Forward)) |
| 81 | SEQ ID NO:1 (CP 2512_2537 Forward) | SEQ ID NO:16 (CP 2650_2677 Reverse) | SEQ ID NO:3 (CP 2542_2568 (Forward)) |
| 82 | SEQ ID NO:11 (CP 2424_2448 Forward) | SEQ ID NO:16 (CP 2650_2677 Reverse) | SEQ ID NO:22 (CP 2542_2568 (Reverse)) |
| 83 | SEQ ID NO:12 (CP 2430_2448 Forward) | SEQ ID NO:16 (CP 2650_2677 Reverse) | SEQ ID NO:22 (CP 2542_2568 (Reverse)) |
| 84 | SEQ ID NO:13 (CP 2472_2498 Forward) | SEQ ID NO:16 (CP 2650_2677 Reverse) | SEQ ID NO:22 (CP 2542_2568 (Reverse)) |
| 85 | SEQ ID NO:14 (CP 2472_2495 Forward) | SEQ ID NO:16 (CP 2650_2677 Reverse) | SEQ ID NO:22 (CP 2542_2568 (Reverse)) |
| 86 | SEQ ID NO:1 (CP 2512_2537 Forward) | SEQ ID NO:16 (CP 2650_2677 Reverse) | SEQ ID NO:22 (CP 2542_2568 (Reverse)) |
| 87 | SEQ ID NO:11 (CP 2424_2448 Forward) | SEQ ID NO:16 (CP 2650_2677 Reverse) | SEQ ID NO:23 (CP 2542_2570 (Reverse)) |
| 88 | SEQ ID NO:12 (CP 2430_2448 Forward) | SEQ ID NO:16 (CP 2650_2677 Reverse) | SEQ ID NO:23 (CP 2542_2570 (Reverse)) |
| 89 | SEQ ID NO:13 (CP 2472_2498 Forward) | SEQ ID NO:16 (CP 2650_2677 Reverse) | SEQ ID NO:23 (CP 2542_2570 (Reverse)) |
| 90 | SEQ ID NO:14 (CP 2472_2495 Forward) | SEQ ID NO:16 (CP 2650_2677 Reverse) | SEQ ID NO:23 (CP 2542_2570 (Reverse)) |
| 91 | SEQ ID NO:1 (CP 2512_2537 Forward) | SEQ ID NO:16 (CP 2650_2677 Reverse) | SEQ ID NO:23 (CP 2542_2570 (Reverse)) |
| 92 | SEQ ID NO:11 (CP 2424_2448 Forward) | SEQ ID NO:16 (CP 2650_2677 Reverse) | SEQ ID NO:24 (CP 2542_2573 (Reverse)) |
| 93 | SEQ ID NO:12 (CP 2430_2448 Forward) | SEQ ID NO:16 (CP 2650_2677 Reverse) | SEQ ID NO:24 (CP 2542_2573 (Reverse)) |
| 94 | SEQ ID NO:13 (CP 2472_2498 Forward) | SEQ ID NO:16 (CP 2650_2677 Reverse) | SEQ ID NO:24 (CP 2542_2573 (Reverse)) |
| 95 | SEQ ID NO:14 (CP 2472_2495 Forward) | SEQ ID NO:16 (CP 2650_2677 Reverse) | SEQ ID NO:24 (CP 2542_2573 (Reverse)) |
| 96 | SEQ ID NO:1 (CP 2512_2537 Forward) | SEQ ID NO:16 (CP 2650_2677 Reverse) | SEQ ID NO:24 (CP 2542_2573 (Reverse)) |
| 97 | SEQ ID NO:11 (CP 2424_2448 Forward) | SEQ ID NO:16 (CP 2650_2677 Reverse) | SEQ ID NO:25 (CP 2545_2568 (Forward)) |
| 98 | SEQ ID NO:12 (CP 2430_2448 Forward) | SEQ ID NO:16 (CP 2650_2677 Reverse) | SEQ ID NO:25 (CP 2545_2568 (Forward)) |
| 99 | SEQ ID NO:13 (CP 2472_2498 Forward) | SEQ ID NO:16 (CP 2650_2677 Reverse) | SEQ ID NO:25 (CP 2545_2568 (Forward)) |
| 100 | SEQ ID NO:14 (CP 2472_2495 Forward) | SEQ ID NO:16 (CP 2650_2677 Reverse) | SEQ ID NO:25 (CP 2545_2568 (Forward)) |
| 101 | SEQ ID NO:1 (CP 2512_2537 Forward) | SEQ ID NO:16 (CP 2650_2677 Reverse) | SEQ ID NO:25 (CP 2545_2568 (Forward)) |

TABLE 2-continued

Exemplary combinations of primers and probes for detecting CT and CTSW

| Combination | Forward Primer | Reverse Primer | Probe |
|---|---|---|---|
| 102 | SEQ ID NO:11 (CP 2424_2448 Forward) | SEQ ID NO:16 (CP 2650_2677 Reverse) | SEQ ID NO:43[3] |
| 103 | SEQ ID NO:12 (CP 2430_2448 Forward) | SEQ ID NO:16 (CP 2650_2677 Reverse) | SEQ ID NO:43[3] |
| 104 | SEQ ID NO:13 (CP 2472_2498 Forward) | SEQ ID NO:16 (CP 2650_2677 Reverse) | SEQ ID NO:43[3] |
| 105 | SEQ ID NO:14 (CP 2472_2495 Forward) | SEQ ID NO:16 (CP 2650_2677 Reverse) | SEQ ID NO:43[3] |
| 106 | SEQ ID NO:1 (CP 2512_2537 Forward) | SEQ ID NO:16 (CP 2650_2677 Reverse) | SEQ ID NO:43[3] |
| 107 | SEQ ID NO:11 (CP 2424_2448 Forward) | SEQ ID NO:15 (CP 2596_2618 Reverse) | SEQ ID NO:21 (CP 2510_2537 (Reverse)) |
| 108 | SEQ ID NO:12 (CP 2430_2448 Forward) | SEQ ID NO:15 (CP 2596_2618 Reverse) | SEQ ID NO:21 (CP 2510_2537 (Reverse)) |
| 109 | SEQ ID NO:13 (CP 2472_2498 Forward) | SEQ ID NO:15 (CP 2596_2618 Reverse) | SEQ ID NO:21 (CP 2510_2537 (Reverse)) |
| 110 | SEQ ID NO:14 (CP 2472_2495 Forward) | SEQ ID NO:15 (CP 2596_2618 Reverse) | SEQ ID NO:21 (CP 2510_2537 (Reverse)) |
| 111 | SEQ ID NO:11 (CP 2424_2448 Forward) | SEQ ID NO:15 (CP 2596_2618 Reverse) | SEQ ID NO:20 (CP 2510_2537 (Forward)) |
| 112 | SEQ ID NO:12 (CP 2430_2448 Forward) | SEQ ID NO:15 (CP 2596_2618 Reverse) | SEQ ID NO:20 (CP 2510_2537 (Forward)) |
| 113 | SEQ ID NO:13 (CP 2472_2498 Forward) | SEQ ID NO:15 (CP 2596_2618 Reverse) | SEQ ID NO:20 (CP 2510_2537 (Forward)) |
| 114 | SEQ ID NO:14 (CP 2472_2495 Forward) | SEQ ID NO:15 (CP 2596_2618 Reverse) | SEQ ID NO:20 (CP 2510_2537 (Forward)) |
| 115 | SEQ ID NO:11 (CP 2424_2448 Forward) | SEQ ID NO:15 (CP 2596_2618 Reverse) | SEQ ID NO:3 (CP 2542_2568 (Forward)) |
| 116 | SEQ ID NO:12 (CP 2430_2448 Forward) | SEQ ID NO:15 (CP 2596_2618 Reverse) | SEQ ID NO:3 (CP 2542_2568 (Forward)) |
| 117 | SEQ ID NO:13 (CP 2472_2498 Forward) | SEQ ID NO:15 (CP 2596_2618 Reverse) | SEQ ID NO:3 (CP 2542_2568 (Forward)) |
| 118 | SEQ ID NO:14 (CP 2472_2495 Forward) | SEQ ID NO:15 (CP 2596_2618 Reverse) | SEQ ID NO:3 (CP 2542_2568 (Forward)) |
| 119 | SEQ ID NO:1 (CP 2512_2537 Forward) | SEQ ID NO:15 (CP 2596_2618 Reverse) | SEQ ID NO:3 (CP 2542_2568 (Forward)) |
| 120 | SEQ ID NO:11 (CP 2424_2448 Forward) | SEQ ID NO:15 (CP 2596_2618 Reverse) | SEQ ID NO:22 (CP 2542_2568 (Reverse)) |
| 121 | SEQ ID NO:12 (CP 2430_2448 Forward) | SEQ ID NO:15 (CP 2596_2618 Reverse) | SEQ ID NO:22 (CP 2542_2568 (Reverse)) |
| 122 | SEQ ID NO:13 (CP 2472_2498 Forward) | SEQ ID NO:15 (CP 2596_2618 Reverse) | SEQ ID NO:22 (CP 2542_2568 (Reverse)) |
| 123 | SEQ ID NO:14 (CP 2472_2495 Forward) | SEQ ID NO:15 (CP 2596_2618 Reverse) | SEQ ID NO:22 (CP 2542_2568 (Reverse)) |
| 124 | SEQ ID NO:1 (CP 2512_2537 Forward) | SEQ ID NO:15 (CP 2596_2618 Reverse) | SEQ ID NO:22 (CP 2542_2568 (Reverse)) |
| 125 | SEQ ID NO:11 (CP 2424_2448 Forward) | SEQ ID NO:15 (CP 2596_2618 Reverse) | SEQ ID NO:23 (CP 2542_2570 (Reverse)) |
| 126 | SEQ ID NO:12 (CP 2430_2448 Forward) | SEQ ID NO:15 (CP 2596_2618 Reverse) | SEQ ID NO:23 (CP 2542_2570 (Reverse)) |
| 127 | SEQ ID NO:13 (CP 2472_2498 Forward) | SEQ ID NO:15 (CP 2596_2618 Reverse) | SEQ ID NO:23 (CP 2542_2570 (Reverse)) |
| 128 | SEQ ID NO:14 (CP 2472_2495 Forward) | SEQ ID NO:15 (CP 2596_2618 Reverse) | SEQ ID NO:23 (CP 2542_2570 (Reverse)) |
| 129 | SEQ ID NO:1 (CP 2512_2537 Forward) | SEQ ID NO:15 (CP 2596_2618 Reverse) | SEQ ID NO:23 (CP 2542_2570 (Reverse)) |
| 130 | SEQ ID NO:11 (CP 2424_2448 Forward) | SEQ ID NO:15 (CP 2596_2618 Reverse) | SEQ ID NO:24 (CP 2542_2573 (Reverse)) |
| 131 | SEQ ID NO:12 (CP 2430_2448 Forward) | SEQ ID NO:15 (CP 2596_2618 Reverse) | SEQ ID NO:24 (CP 2542_2573 (Reverse)) |
| 132 | SEQ ID NO:13 (CP 2472_2498 Forward) | SEQ ID NO:15 (CP 2596_2618 Reverse) | SEQ ID NO:24 (CP 2542_2573 (Reverse)) |
| 133 | SEQ ID NO:14 (CP 2472_2495 Forward) | SEQ ID NO:15 (CP 2596_2618 Reverse) | SEQ ID NO:24 (CP 2542_2573 (Reverse)) |
| 134 | SEQ ID NO:1 (CP 2512_2537 Forward) | SEQ ID NO:15 (CP 2596_2618 Reverse) | SEQ ID NO:24 (CP 2542_2573 (Reverse)) |
| 135 | SEQ ID NO:11 (CP 2424_2448 Forward) | SEQ ID NO:15 (CP 2596_2618 Reverse) | SEQ ID NO:25 (CP 2545_2568 (Forward)) |
| 136 | SEQ ID NO:12 (CP 2430_2448 Forward) | SEQ ID NO:15 (CP 2596_2618 Reverse) | SEQ ID NO:25 (CP 2545_2568 (Forward)) |
| 137 | SEQ ID NO:13 (CP 2472_2498 Forward) | SEQ ID NO:15 (CP 2596_2618 Reverse) | SEQ ID NO:25 (CP 2545_2568 (Forward)) |
| 138 | SEQ ID NO:14 (CP 2472_2495 Forward) | SEQ ID NO:15 (CP 2596_2618 Reverse) | SEQ ID NO:25 (CP 2545_2568 (Forward)) |
| 139 | SEQ ID NO:1 (CP 2512_2537 Forward) | SEQ ID NO:15 (CP 2596_2618 Reverse) | SEQ ID NO:25 (CP 2545_2568 (Forward)) |

TABLE 2-continued

Exemplary combinations of primers and probes for detecting CT and CTSW

| Combination | Forward Primer | Reverse Primer | Probe |
|---|---|---|---|
| 140 | SEQ ID NO:11 (CP 2424_2448 Forward) | SEQ ID NO:15 (CP 2596_2618 Reverse) | SEQ ID NO:43[3] |
| 141 | SEQ ID NO:12 (CP 2430_2448 Forward) | SEQ ID NO:15 (CP 2596_2618 Reverse) | SEQ ID NO:43[3] |
| 142 | SEQ ID NO:13 (CP 2472_2498 Forward) | SEQ ID NO:15 (CP 2596_2618 Reverse) | SEQ ID NO:43[3] |
| 143 | SEQ ID NO:14 (CP 2472_2495 Forward) | SEQ ID NO:15 (CP 2596_2618 Reverse) | SEQ ID NO:43[3] |
| 144 | SEQ ID NO:1 (CP 2512_2537 Forward) | SEQ ID NO:15 (CP 2596_2618 Reverse) | SEQ ID NO:43[3] |
| 145 | SEQ ID NO:5 (CP 1223_1249 Forward) | SEQ ID NO:10 (CP 1399_1424 Reverse) | SEQ ID NO:43[3] |

TABLE 2-continued

Exemplary combinations of primers and probes for detecting CT and CTSW

| Combination | Forward Primer | Reverse Primer | Probe |
|---|---|---|---|
| 146 | SEQ ID NO:6 (CP 1224_1249 Forward) | SEQ ID NO:10 (CP 1399_1424 Reverse) | SEQ ID NO:27[2] |
| 147 | SEQ ID NO:7 (CP 1233_1256 Forward) | SEQ ID NO:10 (CP 1399_1424 Reverse) | SEQ ID NO:27[2] |
| 148 | SEQ ID NO:8 (CP 1269_1295 Forward) | SEQ ID NO:10 (CP 1399_1424 Reverse) | SEQ ID NO:27[2] |
| 149 | SEQ ID NO:9 (CP 1272_1295 Forward) | SEQ ID NO:10 (CP 1399_1424 Reverse) | SEQ ID NO:27[2] |
| 150 | SEQ ID NO:5 (CP 1223_1249 Forward) | SEQ ID NO:36[1] | SEQ ID NO:27[2] |
| 151 | SEQ ID NO:6 (CP 1224_1249 Forward) | SEQ ID NO:36[1] | SEQ ID NO:27[2] |
| 152 | SEQ ID NO:7 (CP 1233_1256 Forward) | SEQ ID NO:36[1] | SEQ ID NO:27[2] |

TABLE 2-continued

Exemplary combinations of primers and probes for detecting CT and CTSW

| Combination | Forward Primer | Reverse Primer | Probe |
|---|---|---|---|
| 153 | SEQ ID NO:8 (CP 1269_1295 Forward) | SEQ ID NO:36[1] | SEQ ID NO:27[2] |
| 154 | SEQ ID NO:9 (CP 1272_1295 Forward) | SEQ ID NO:36[1] | SEQ ID NO:27[2] |

[1]SEQ ID NO:26 is cagagtacat cggtcaacga aga (23) (Rickett et al., 2005)
[2]SEQ ID NO:27 is ccccaccatt tttccggagc ga (22) (Rickett et al., 2005)
[2]SEQ ID NO:43 is cgatgatttg agcgtgtgta gcgg (24)

Probes

In addition to the sequences listed as "probes" in Table 2, probes can comprise any portion of SEQ ID NO:44, the region amplified when SEQ ID NOs:1 and 2 are used as amplification primers, or complements thereof. The probes are usually n, consecutive nucleotides of SEQ ID NO:44, or complements thereof, wherein 10≤n≤140. SEQ ID NO:44 is:

(SEQ ID NO:44)
caagcttaga tccgtttctc atacggtttt cctcgatgat ttgagcgtgt gtagcgctga    60
agaaaatttg agcaatttca ttttccgctc gtttaatgag tacaatgaaa atccattgcg   120
tagatctccg tttctattgc                                               140

Furthermore, probes can deviate from the sequence of SEQ ID NO:44 or a portion thereof, without substantially impairing sensitivity or detection. Probes can therefore have a nucleotide sequence wherein the probe has 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence of SEQ ID NO:44 or a complement thereof, or a portion thereof, or complements of these portions. Because probes can be modified sequences, e.g., additional nucleotides are added to the 3' and/or 5' termini to facilitate secondary structure formation (e.g., stem-loops) or interspersed within the sequence of SEQ ID NO:44, the probe sequence can then be even less than 70% identical with the sequence of SEQ ID NO:44 and the assay substantially retains sensitivity.

Likewise, primers can deviate from the sequences presented in Table 2 without substantially impairing sensitivity.

Amplifying CT and CTSW Targets

The amplification method generally comprises (a) a reaction mixture comprising nucleic acid amplification reagents, at least one primer/probe set of the present invention, and a test sample suspected of containing a at least one target sequence; and (b) subjecting the mixture to amplification conditions to generate at least one copy of a nucleic acid sequence complementary to the target sequence if the target sequence is present.

Step (b) of the above methods can be repeated any suitable number of times prior to, for example, a detection step; e.g., by thermal cycling the reaction mixture between 10 and 100 times, typically between about 20 and about 60 times, more typically between about 25 and about 45 times.

Nucleic acid amplification reagents include enzymes having polymerase activity, enzyme co-factors, such as magnesium or manganese; salts; nicotinamide adenine dinucleotide (NAD); and deoxynucleotide triphosphates (dNTPs), (dATP, dGTP, dCTP and dTTP).

Amplification conditions are those that promote annealing and extension of one or more nucleic acid sequences. Such annealing is dependent in a rather predictable manner on several parameters, including temperature, ionic strength, sequence length, complementarity, and G:C content of the sequences. For example, lowering the temperature in the environment of complementary nucleic acid sequences promotes annealing. Typically, diagnostic applications use hybridization temperatures that are about 2° C. to 18° C. (e.g., approximately 10° C.) below $T_m$. Ionic strength also impacts $T_m$. Typical salt concentrations depend on the nature and valency of the cation but are readily understood by those skilled in the art. Similarly, high G:C content and increased sequence length also stabilize duplex formation. Generally probes of about 30 bp or less and having a high G:C content work well.

Finally, the hybridization temperature is selected close to or at the $T_m$ of the primers or probe. Thus, obtaining suitable hybridization conditions for a particular primer/probe set is well within ordinary skill of the PCR arts.

The primer sequences (SEQ ID NOs:1, 2 and 5-16) of any particular primer/probe set can be used as amplification primers.

In one embodiment, the detection method generally comprises (a) forming a reaction mixture comprising nucleic acid amplification reagents, at least one primer/probe set of the present invention, and a test sample suspected of containing at least one target sequence; (b) subjecting the mixture to amplification conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of the target sequence (CT and CTSW and/or a control sequence) in the sample.

Specific amplicons produced by target nucleic acid sequence amplification using the polynucleotides of the present invention can be detected by any method known in the art. For example, one or more of the primers used in the amplification reactions can be labeled such that an amplicon can be directly detected by conventional techniques subsequent to the amplification reaction. Alternatively, a labeled probe consisting of one of the primers used in the amplification reaction, or a third polynucleotide distinct from the primer sequences that has been labeled and is complementary to a region of the amplified sequence, can be added after the amplification reaction is complete. The probe is allowed to hybridize, any complexes washed, and the label is detected. One skilled in the art will understand that, as outlined above, step b) of the above method can be repeated several times prior to step (c) by thermal cycling the reaction mixture by standard techniques known in the art.

Any amplification product can be detected during or subsequently to amplification. Methods for detecting the amplification of a target sequence during amplification are described above and by Gelfand et al. (Gelfand et al., 1993). Gel electrophoresis can be used to detect amplified products, as well as an approximation of the size of any amplified segments. Alternatively, amplification products are hybridized to probes, then separated from other reaction components and detected using microparticles and labeled probes.

A procedure that allows both amplification and detection of target nucleic acid sequences to take place concurrently in a single closed reaction vessel is advantageous. Such a procedure avoids the risk of "carry-over" contamination in post-amplification processing steps, allows high-throughput assays and automated procedures. Furthermore, this type of procedure allows "real-time" monitoring of the amplification reaction as well as more conventional "end-point" monitoring.

The present invention includes the use of the polynucleotides of SEQ ID NOs:1-3 and 5-25 in methods to specifically amplify and detect target nucleic acid sequences in a test sample in a single vessel format. In one embodiment, an intercalating dye (e.g., SYBR Green) or an antibody that specifically binds the amplified sequence is added to the reaction vessel. In another embodiment, a third polynucleotide distinct from the primer sequences, which is complementary to a region of the amplified sequence, can be included in the reaction, as a probe.

For use in assays in which both amplification with primers and detection of target with a probe occur concurrently in a single closed reaction vessel, the probe possesses certain properties. For example, because the probe is present during the amplification reaction, the probe should not interfere with the reaction and should also be stable under the reaction conditions. For real-time detection, the probe should bind its target sequence under amplification conditions and emit a signal only upon binding the target sequence. Examples of probe molecules that are particularly well-suited to this type of procedure include molecular beacon probes, TAQMAN® probes and linear probes, such as those described by Abravaya et al. (Abravaya et al., 2005).

TAQMAN® probes are dual-labeled, fluorogenic nucleic acid probes composed of a polynucleotide complementary to the target sequence that is labeled at one terminus with a fluorophore and at the other terminus with a quencher. TAQMAN® probes can be used as real-time probes in amplification reactions. As constructed, the close proximity of the fluorophore and the quencher ensures that the fluorophore is internally quenched. During extension, the probe is cleaved by the 5' nuclease activity of the polymerase and the fluorophore is released. The released fluorophore is no longer quenched and thus produces a detectable signal.

Molecular beacons are polynucleotide probes that form stem-loop (hairpin) structures. The loop is single-stranded and contains sequences complementary to the target sequence, whereas the stem typically is unrelated to the target sequence and self-hybridizes to form a double-strand. Nucleotides that are both complementary to the target sequence and can self-hybridize can also form part of the stem region. Attached to one arm of the stem is a fluorophore moiety, and to the other arm a quencher moiety. When the polynucleotide forms a hairpin, the fluorophore and the quencher are in close proximity and the fluorophore is quenched. Upon binding to the target sequence, the fluorophore and the quencher become separated and the fluorophore is no longer quenched producing a detectable signal. In one embodiment, the probes are molecular beacon probes that comprise polynucleotides of the present invention together with flanking self-complementary regions. The polynucleotides of the present invention can make up the loop region of the molecular beacon, or they can make up the loop region and part of the stem region. Thus, the self-complementary stem sequences can be unrelated to the target sequence or can be partially complementary to the target sequence.

The polynucleotides of the invention can also be used as linear probes with a fluorophore and a high-efficiency quencher, such as the Black Hole Quenchers (BHQ®; Biosearch Technologies, Inc.; Novato, Calif., USA). The high quenching efficiency and lack of native fluorescence of the BHQ® dyes allow "random-coil" quenching to occur in linear probes labeled at one terminus with a fluorophore and at the other with a BHQ® dye, thus ensuring that the fluorophore does not fluoresce when the probe is in solution. Upon binding its target sequence, the probe stretches out, the fluorophore and quencher are thus spatially separated and the fluorophore is no linger quenched. The BHQ® dyes can also be used as the quencher moiety in molecular beacon or TAQMAN® probes.

Suitable fluorophores and quenchers for use with the polynucleotides of the present invention can be readily determined Marras et al., 1999; Tyagi et al., 1998). Many fluorophores and quenchers are available commercially, for example, from Molecular Probes Eugene, Oreg., USA) or Biosearch Technologies, Inc. (Novato, Calif., USA.). Examples of useful fluorophores include fluorescein and fluorescein derivatives such as a dihalo-($C_1$ to $C_8$)dialkoxy-carboxyfluorescein, 5-(2'-aminoethyl)aminonaphthalene-1-sulphonic acid (EDANS), coumarin and coumarin derivatives, N-(2-aminoethyl)-4-amino-3,6-disulfo-1,8-naphthalimide dipotassium salt (Lucifer yellow), Sulforhodamine 101 sulfonyl chloride TEXAS RED®), tetramethylrhodamine, tetrachloro-6-carboxyfluoroscein, 5-carboxyrhodamine, cyanine dyes and derivatives, etc. Examples of quenchers include DABCYL, 4'-(4-dimethylaminophenylazo)benzoic acid (DABSYL), 4-dimethylaminophenylazophenyl-4-dimethylaminophenylazophenyl-4'-maleimide (DABMI), tetramethylrhodamine, carboxytetramethylrhodamine (TAMRA), BHQ® dyes and the like. Metallic nano-particles can be used to enhance any fluorescent signal, such as those made of gold and silver. They can likewise be tagged with targeting molecules such that they are in close proximity of the stained DNA. QDs can also be used.

Primer selection for use with the molecular beacon probe requires certain criteria to be met. For example, it is important that there are no areas of complementarity that may cause the molecular beacon to bind to a primer that results in a high background signal.

The polynucleotides according to the present invention, therefore, are further provided in combinations, comprising two primers and at least one probe, that can be used to specifically amplify and detect target nucleic acid sequences in a test sample. In a related embodiment, primer/probe sets are provided for the amplification and detection of target nucleic acid sequences by molecular beacon PCR.

Molecular beacon probes can be used to monitor the progress of an amplification reaction in real time. During the course of an amplification reaction, the molecular beacon interacts with its target sequence at the annealing temperature for the probe, and a fluorescent signal is generated. As the number of target strands produced in the amplification reaction increases, the number of molecular beacons bound to their target increases concomitantly, as does the strength of the fluorescent signal.

In accordance with the present invention, therefore, combinations of two primers and at least one probe can be used in either detection, in which the strength of the detectable signal is measured at the conclusion of the amplification reaction, or in real-time detection, in which the signal is monitored throughout the amplification reaction.

Multiple, Simultaneous Amplicon Detection

CT primers can be used in conjunction with primers for the amplification of other markers for disease, such as *Neisseria gonorrhoeae* (NG) to amplify target sequences from either or both organisms in a single amplification reaction. The co-amplification reaction, followed by species-specific hybridization reactions, allow for concurrent assessment of a test sample for infection with either CT, or NG, or both organisms. Both NG and either CT or CTSW (or both CT and CTSW) can be amplified and/or detected simultaneously in a single reaction mixture using a combination of primer/probe sets (e.g., one selected from the CT specific primer/probe sets and another selected from the NG-specific primer/probe sets; examples are shown in Table 3). Of course, each probe is detectably distinct from each of the other probe(s). For example if two or more probes are present in the same reaction mixture, the fluorophore moieties of each probe should fluoresce at different wavelengths.

TABLE 3

CT and NG Sequences

| SEQ ID NO: | Name | Sequence |
|---|---|---|
| 28 | CT Forward | gggattcctg taacaacaag tcagg |
| 29 | CT Alternative Forward | ctgggattcd tgtaacaaca agtcagg |
| 30 | CT Alternative 2 Forward | gggattcgtg taacaacaag tcagg |
| 31 | CT Reverse | gcttgcacga agtactctag gag |
| 32 | CT Probe | atagcactat agaactctgc aa |
| 33 | CT Alternative Probe | catagcacta tagaactctg caagcc |
| 34 | CT Beacon Probe[1] | ctggcatagc actatagaac tctgcaagcc ag |
| 35 | NG Forward | cgacgtaccg gttttgttc |
| 36 | NG Reverse | cggctcctta ttcggtttga cc |
| 37 | NG Probe | acaccgcccg gaacccga |
| 38 | NG Alternative Probe | gaaacaccgc ccggaacccg at |
| 39 | NG Beacon Probe 2 | ctcggacacc gcccggaacc cgag |

[1]Contains non-bacterial, self-complementary bases (residues 1-5 and 28-32) so as to form a stem of a beacon probe under suitable conditions with residues 1-5 and 28-32.
[2]Contains non-bacterial, self-complementary bases (residues 1-5 and 24) so as to form a stem of a beacon probe under suitable conditions with residues 1-5 and 20-24.

In one embodiment, the invention is drawn to a combination of polynucleotide reagents useful for amplifying and/or detecting CT and CTSW comprising a first and a second polynucleotide, wherein the first polynucleotide consists essentially of a nucleic acid sequence having at least 70%, 80%, 90%, 95%, or 100% sequence identity with a polynucleotide of SEQ ID NOs:1, 5-9, 11-13 or 14, and complements thereof; and the second polynucleotide consists essentially of a nucleic acid sequence having at least 70%, 80%, 90%, 95%, or 100% sequence identity with a polynucleotide of SEQ ID NOs:2, 10, 15, 16 and 26, and complements thereof. The first and second polynucleotides can serve as primers in an amplification reaction. The combination of polynucleotide reagents can further include a third polynucleotide having at least 70%, 80%, 90%, 95%, or 100% sequence identity with a polynucleotide selected from the group consisting of SEQ ID NOs:3, 17-25, 27, 42 and a polynucleotide comprising n nucleotides, wherein 10≤n≤140 consecutive nucleotides of SEQ ID NO:44, and complements thereof. The third polynucleotide can serve as a probe for hybridizing and detecting a sequence amplified by the polynucleotides of SEQ ID NOs: 1, 2, 5-14, 16 and 26 (or complements thereof) in an amplification reaction, for example.

The invention also include additional embodiments, wherein the combination of polynucleotide reagents of the first and second embodiments listed above further comprise a fourth, fifth and sixth polynucleotides, wherein the combination is useful for detecting and/or amplifying CT and CTSW, and wherein the fourth polynucleotide consists essentially of a nucleic acid sequence having at least 70%, 80%, 90%, 95%, or 100% sequence identity with a polynucleotide selected from the group consisting of SEQ ID NOs:28-30 and complements thereof; the fifth polynucleotide consists essentially of a nucleic acid sequence having at least 70%, 80%, 90%, 95%, or 100% sequence identity with a polynucleotide selected from the group consisting of SEQ ID NO:31 and a complement thereof; and the sixth polynucleotide consists essentially of a nucleic acid sequence having at least 70%, 80%, 90%, 95%, or 100% sequence identity with a polynucleotide selected from the group consisting of SEQ ID NOs:32-34 and complements thereof. To distinguish CT from CTSW, the probes of SEQ ID NOs3, 17-25, 27, 42 and 44 can be labeled with a detectable label which signal emits at a different wavelength than a detectable label on the probes of SEQ ID NOs: 32-34.

The invention also includes another embodiment, wherein the combination of polynucleotide reagents of the first and second embodiments listed above further comprise a fourth, fifth and sixth polynucleotides, the combination useful for detecting and/or amplifying CT, CTSW and NG, wherein the fourth polynucleotide consists essentially of a nucleic acid sequence having at least 70%, 80%, 90%, 95%, or 100% sequence identity with a polynucleotide of SEQ ID NO:35 and a complement thereof; the fifth polynucleotide consists essentially of a nucleic acid sequence having at least 70%, 80%, 90%, 95%, or 100% sequence identity with a polynucleotide of SEQ ID NO:36 and a complement thereof; and the sixth polynucleotide consists essentially of a nucleic acid sequence having at least 70%, 80%, 90%, 95%, or 100% sequence identity with a polynucleotide selected from the group consisting of SEQ ID NOs:37-39 and complements thereof. To distinguish CT from CTSW, the probes of SEQ ID NOs3, 17-25, 27, 42 and 44 can be labeled with a detectable label which signal is given off at a different wavelength than a detectable label on the probes of SEQ ID NOs:32-34; and furthermore, the NG probes of SEQ ID NOs:37-39 can include yet a third detectable label that emits at a different wavelength than the probes for CT and CTSW.

The invention also includes another embodiment, wherein the combination of polynucleotide reagents of the first and second embodiments just listed above further comprise a fourth, fifth, sixth, seventh, eighth and ninth polynucleotides, the combination useful for detecting and/or amplifying CT, CTSW and NG, the fourth polynucleotide consists essentially of a nucleic acid sequence having at least 70%, 80%, 90%, 95%, or 100% sequence identity with a polynucleotide selected from the group consisting of SEQ ID NOs:28-30 and complements thereof; the fifth polynucleotide consists essentially of a nucleic acid sequence having at least 70%, 80%, 90%, 95%, or 100% sequence identity with a polynucleotide of SEQ ID NO:31 and complements thereof; the sixth polynucleotide consists essentially of a nucleic acid sequence having at least 70%, 80%, 90%, 95%, or 100% sequence identity with a polynucleotide selected from the group consisting of SEQ ID NOs:32, 33 and 34 and complements thereof; the seventh polynucleotide consists essentially of a nucleic acid sequence having at least 70%, 80%, 90%, 95%, or 100% sequence identity with a polynucleotide of SEQ ID NO:35 or a complement thereof; the eighth polynucleotide consists essentially of a nucleic acid sequence having at least 70%, 80%, 90%, 95%, or 100% sequence identity with a polynucleotide of SEQ ID NO:36 or a complement thereof; and the ninth polynucleotide consists essentially of a nucleic acid sequence having at least 70%, 80%, 90%, 95%, or 100% sequence identity with a polynucleotide selected from the group consisting of SEQ ID NOs: 37, 38 and 39 and complements thereof. To distinguish CT from CTSW, the probes of SEQ ID NOs:3, 17-25, 27, 42 and 44 can be labeled with a detectable label which signal is given off at a different wavelength than a detectable label on the probes of SEQ ID NOs: 32-34; and furthermore, the NG probes of SEQ ID NOs:37-39 can include yet a third detectable label that emits at a different wavelength than the probes for CT and CTSW.

In other embodiments, at least one polynucleotide reagent can include a detectable label or a quencher.

In other embodiments, the invention includes kits that include the combination of polynucleotides of the embodiments listed above, the kit also including amplification reagents.

In yet other embodiments, the invention includes methods of amplifying and/or detecting CT, CTSW and/or NG, using the combination of polynucleotide reagents of embodiment 1-5 listed above. These reactions can further include at least one control polynucleotide, positive and/or negative, as well as for those that can be used for normalization. However, when detecting CT or CTSW, if the reaction consists of 7.5 units of a DNA polymerase, 15 mM Tris-HCl, pH 8.0, 50 mM KCl, 9.5 mM MgCl$_2$, 0.2 mM dNTPs, 500 nM of the first and second polynucleotides and 60 nM ROX, then if the first polynucleotide consists of a nucleic acid sequence of SEQ ID NO:1 or a complement thereof, then the second polynucleotide does not consist of a nucleic acid sequence of SEQ ID NO:16 or a complement thereof, and the third polynucleotide does not consist of a nucleic acid sequence of SEQ ID NO:23 or complement thereof;

if the first polynucleotide consists of a nucleic acid sequence of SEQ ID NO:1 or a complement thereof, then the second polynucleotide does not consist of a nucleic acid sequence of SEQ ID NO:2 or a complement thereof, and the third polynucleotide does not consist of a nucleic acid sequence of SEQ ID NO:22 or a complement thereof if the first polynucleotide consists of a nucleic acid sequence of SEQ ID NO:8 or 9 or complements thereof, then the second polynucleotide does not consist of a nucleic acid sequence SEQ ID NOs:10 or 26 or complements thereof, and the third polynucleotide does not consist of a nucleic acid sequence of SEQ ID NO:17 or a complement thereof;

if the first polynucleotide consists of a nucleic acid sequence of SEQ ID NO:5 or 6 or complements thereof, then the second polynucleotide does not consist of a nucleic acid sequence of SEQ ID NO:10 or a complement thereof, and the third polynucleotide does not consist of a nucleic acid sequence of SEQ ID NO:19 or a complement thereof; and if the first polynucleotide consists of a nucleic acid sequence of SEQ ID NO:14 or a complement thereof, then the second polynucleotide does not consist of a nucleic acid sequence of SEQ ID NO:2 or a complement thereof, and the third polynucleotide does not consist of a nucleic acid sequence of SEQ ID NO:22 or complement thereof.

Quantification

The polynucleotides of SEQ ID NOs:1-3 and 5-25 can also be used in assays to quantify CT and CTSW nucleic acids. Thus, the polynucleotides according to the present invention can be used in a method to specifically amplify, detect and quantitate target nucleic acid sequences in a test sample.

Controls

Various types of standards for quantitative assays are available. For example, the standard can consist of a standard curve compiled by amplification and detection of known quantities of CT or CTSW nucleic acids under assay conditions. Alternatively, an internal standard can be included in the reaction. Such internal standards generally comprise a control target nucleic acid sequence and a control polynucleotide probe. The internal standard can optionally further include an additional pair of primers. The primary sequence of these control primers can be unrelated to the polynucleotides of the present invention and specific for the control target nucleic acid sequence. Alternatively, no additional primer need be used if the control target sequence is designed such that it binds at one end with a primer from a first primer/probe set directed to a first target sequence (for example, CT), and binds at the other end with a primer for a second primer/probe set directed to a second target sequence (for example, NG), such that copies will be generated under amplifying conditions.

In the context of the present invention, a control target nucleic acid sequence is a nucleic acid sequence that:

(a) can be amplified either by a CT or CTSW primer or primer pair being used in a particular reaction or by distinct control primers;

(b) specifically hybridizes to the control probe under suitable conditions; and (c) does not hybridize with a CT- or CTSW-specific probe under the same conditions.

In the context of the present invention, in addition to fulfilling the standard requirements for probe molecules, the control polynucleotide probe for use in quantitation reactions:

(a) specifically hybridizes to the control sequence under suitable conditions;

(b) does not hybridize with a CT or CTSW sequence, to the CT or CTSW-specific probe, or to the CT or CTSW-specific primers under the same conditions, when a CT or CTSW target sequence is being detected;

(c) incorporates a detectable label that is distinct from the label incorporated into other probes used in the same reaction mixture.

The actual nucleic acid sequence of the control target nucleic acid and the control probe is not important provided that they both meet the criteria outlined above.

The amount of target nucleic acid in a test sample can be quantified using "end point" methods or "real time" methods. When the polynucleotides of SEQ ID NOs:1-3 and 5-25 are used as probes in quantitative assays, they can be used as conventional hybridization probes, linear BHQ® probes, TAQMAN® probes, molecular beacon probes, or combinations or modified versions thereof.

High-Throughput Assays

For high-throughput assays, reaction components are usually housed in a multi-container carrier or platform, such as a multi-well microtiter plate, that allows a plurality of assay reactions containing different test samples to be monitored in the same assay. The present invention also contemplates highly automated, high-throughput assays to increase the efficiency of the screening or assay process. Many high-throughput systems are now available commercially, as are automation capabilities for many procedures, such as sample and reagent pipetting, liquid dispensing, timed incubations, formatting samples into microarrays, microplate thermocycling and microplate readings in an appropriate detector, resulting in much faster throughput times.

Kits

The polynucleotides of SEQ ID NOs:1-3 and 5-25 can be included as part of kits that allow for the detection and/or quantitation of CT and CTSW nucleic acids. Such kits comprise one or more of the polynucleotides of the invention for use as a primer and/or probe. In one embodiment of the present invention, the polynucleotides are provided in the kits in combinations for use as primers to specifically amplify CT and CTSW nucleic acids in a test sample, as shown in Table 2.

Kits for the detection of CT and CTSW nucleic acids can also include a control target nucleic acid and a control polynucleotide probe. Kits can also include control primers, which specifically amplify a control target nucleic acid sequence.

Kits can also include amplification reagents, reaction components and/or reaction vessels. One or more of the polynucleotides can incorporate a detectable label. Kits can also include reagents for labeling the polynucleotides. One or more of the components of the kit may be lyophilized, and the kit can further include reagents suitable for reconstituting the lyophilized products. The kit can additionally contain instructions for use.

When a kit is supplied, the different components of the composition may be packaged in separate containers and admixed immediately before use. Such packaging of the components separately may permit long-term storage of the active components. For example, one or more of the particles having polynucleotides attached thereto; the substrate; and the nucleic acid enzyme are supplied in separate containers.

The reagents included in the kits can be supplied in containers of any sort such that the different components are preserved and are not adsorbed or altered by the materials of the container. For example, sealed glass ampules can contain one or more of the reagents or buffers that have been packaged under a neutral, non-reacting gas, such as nitrogen. Ampules can consist of any suitable material, such as glass, organic polymers, such as polycarbonate, polystyrene, etc.; ceramic, metal or any other material typically used to hold similar reagents. Other examples of suitable containers include simple bottles that can be fabricated from similar substances as ampules, and envelopes, that can have foil-lined interiors, such as aluminum or an alloy. Other containers include test tubes, vials, flasks, bottles, syringes, etc.

Kits can also be supplied with instructional materials. Instructions may be printed on paper or other substrate, and/or may be supplied as an electronic-readable medium, such as a floppy disc, CD-ROM, DVD-ROM, Zip disc, videotape, audiotape, etc.

The polynucleotides, methods, and kits of the present invention are useful in clinical or research settings for the detection and/or quantitation of CT and CTSW nucleic acids. Thus, in these settings the polynucleotides can be used in assays to diagnose CT and CTSW infection in a subject, or to monitor the quantity of a CT and CTSW target nucleic acid sequence in a subject infected with CT and CTSW. Monitoring the quantity of bacteria in a subject is particularly important in identifying or monitoring response to anti-bacterial therapy, although because the assays can detect bacteria that has recently died, it is important to time the assay relative to the therapeutic intervention.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1

Screening Candidate CTSW Primer/Probe Combinations

Newly designed primer/probes were tested at different combinations for specific amplification and detection of CT. In total, twenty seven sequences were tested as primers or probes and included SEQ ID NO:1-3, 5-25, 26, 27 and 43 (Table 1). One hundred fifty four sets of different combinations were made (Table 2). All candidate probes were labeled with QUASAR™ Q670 (BioSearch Technologies, Inc.; Novato, Calif.) (a CY5™ replacement; Biosearch Technologies; Novato, Calif.; USA) and BHQ-2™ (BioSearch Technologies) as a quencher with the exception of SEQ ID NO:43. The latter was labeled with 6-carboxy-fluorescein (FAM™; Applied Biosystems; Foster, Calif.; USA) and BHQ-1™ (Applied Biosystems) as a quencher. Several different dilutions of CT genomic DNA preparation were made and used as target, and CT/NG negative diluent was used negative control for each set of primer/probe.

A master mix was prepared for each primer/probe combination (7.5 U AMPLITAQ™ Gold, 15 mM Tris-HCl, pH 8.0, 50 mM KCl, 9.5 MgCl$_2$, 0.2 mM dNTPs, 500 nM of each tested primer, 200 nM probe and 60 nM ROX. The samples were loaded into the optical reaction plate and sealed. The plate was then loaded into the cycler/reader device and subjected to cycling conditions as specified in Example 2.

PCR cycling conditions for all examples included a cycle of 95° C. for 570 seconds, and then 45 cycles of 92° C. for 10 seconds, 58° C. for 30 seconds, and 65° C. for 60 seconds. The device that was used for PCR and real time detection was the Abbott m2000rt cycler/reader (an integrated REALTIME™ PCR amplification and detection instrument).

Under the tested PCR component concentration and the cycling condition, 145 different primer/probe combinations out of a total 154 gave robust, real-time amplification and detection. The remaining nine combinations either generated no amplification curves, gave ambiguous results, had poor signal:noise ratios, or were not replicable. These nine combinations were 4, 5, 11, 12, 19, 20, 47, 48 and 94, which would require further optimization.

Example 2

Testing CTSW Primer/Probe

In this example, newly designed primer/probe sets designed to accommodate the newly discovered Swiss CT deletion variant was tested for specificity and robustness against the current CT/NG oligonucleotide reagents provided in the Abbott Laboratories (Abbott Park, Ill., USA) REALTIME™ CT/NG diagnostic kit. The CT/NG oligonucleotide reagent contains 6 primers and 3 probes primers for CT, NG and an internal control (IC), and probes for CT, NG and IC). The original CT probe was labeled with 6-carboxy-fluorescein FAM™; Applied Biosystems; Foster, Calif.; USA). The candidate probes used QUASAR™ Q670 (a CY5™ replacement; BioSearch Technologies; Novato, Calif.; USA) as fluorophore and BHQ-2™ (BioSearch Technologies) as a quencher.

The primer and probe sequences for the current CT/NG are shown in Table 4.

TABLE 4

Reagents for a current commercial embodiment of CT/NG detection assay

| Oligonucleotide | SEQ ID NO: | Labels |
|---|---|---|
| CT primer forward | 28 | NA |
| CT primer reverse | 31 | NA |
| CT probe | 33 | 5'-FAM ™[1]; 3'-BHQ-1 ™ |
| NG primer forward | 35 | NA |
| NG primer reverse | 36 | NA |
| NG probe | 37 | 5'-VIC ™[2]; 3'-BHQ-1 ™ |
| IC primer forward | 40 | NA |
| IC primer reverse | 41 | NA |
| IC probe | 42 | 5'-NED ™[3]; BHQ-2 ™ |

[1]FAM ™ (excitation 495 nm; emission at 515 nm)
[2]VIC ™ (excitation at 535 nm; emission at 555 nm)
[3]NED ™ (excitation at 550 nm; emission at 570 nm)

The candidate primers for detecting CT and CTSW were SEQ ID NOs:1 and 2, and the probe was SEQ ID NO:3. SEQ ID NO:3 was labeled at the 5' end with QUASAR™ Q670 and the quencher BHQ-2™ at the 3' end. Table 5 below summarizes the reagents used in this and all assays described in these Examples (as necessary).

TABLE 5

Summary of reagents used in the Examples (unless otherwise noted)

| Reagent (All Abbott Laboratories, unless Otherwise noted) | Catalog number |
|---|---|
| 96 well Optical Reaction Plate with Bar Code (code 128) (ABI Prism; Foster City, CA; USA) | 4J71-70 |
| CT/NG Activation Reagent (Abbott Laboratories) (MgCl$_2$, Tris buffer pH 8.0, KCl, EDTA, and EGTA) | 2G28M0099 |
| CT/NG Amplification Reagent Fill/Label (Abbott Laboratories) (Tris buffer pH 8.0, 6 primers and 3 probes (see Table 4), ROX (carboxy-X-rhodamine), dNTP, KCl, EDTA, and EGTA) ("CT/NG reaction mix") | 2G28L0099 |
| CT genomic DNA prep (in-house) | N/A |
| CT/NG Cutoff Control (linearized plasmids containing CT and NG targets at designated concentrations in TE[1] pH 8.0 and salmon testes DNA as carrier) | 2G28A |
| CT/NG Enzyme Reagent (Abbott Laboratories) (AMPLITAQ ™ Gold) | 337940099 |

TABLE 5-continued

Summary of reagents used in the Examples (unless otherwise noted)

| Reagent (All Abbott Laboratories, unless Otherwise noted) | Catalog number |
|---|---|
| CT/NG Negative Diluent (Abbott Laboratories) (TE buffer pH 8.0 and salmon testes DNA as carrier) | 31980 |
| CT/NG PCR Internal Control (IC; Abbott Laboratories) (linearized plasmid containing a pumpkin sequence unrelated to the CT/NG analyte in TE pH 8.0 and salmon testes DNA as carrier) | 8100/2G28Y |
| Deep well tray (ABI Prism) | 04J71-30 |
| DNA Sample Preparation System | 06K11-24 |
| Reaction Vessel (Sarstedt; Newton, NC, USA) | 55.526.044 |

[1]TE = 10 mM Tris-HCl/1 mM EDTA

TABLE 6

Summary of PCR components and concentrations[1]

| Component | Final concentration |
|---|---|
| AMPLITAQ ™ Gold | 7.5 Units |
| Tris-HCl, pH 8.0 | 15 mM |
| KCl | 50 mM |
| $MgCl_2$ | 9.5 mM |
| dNTP | 0.6 mM each |
| PCR primers (CT, NG, IC and candidate CT) | 500 nM each |
| Probes (CT, NG, IC and candidate CT) | 200 nM each |
| ROX | 75 nM |

[1]Final reaction volume was 50 µl.

PCR cycling conditions for all examples included a cycle of 95° C. for 570 seconds, and then 45 cycles of 92° C. for 10 seconds, 58° C. for 30 seconds, and 65° C. for 60 seconds. The device that was used for PCR and real time detection was the Abbott m2000rt cycler/reader (an integrated REALTIME™ PCR amplification and detection instrument).

Twenty-four CTSW clinical isolates from Sweden were tested. DNA was purified from clinical samples using methods known in the art and supplied to Abbott Laboratories. In this Example, the reagents from the REALTIME™ CT/NG diagnostic kit (Table 4) were spiked with the CTSW primers and probe.

A master mix was prepared and contained a total of 8 primers and 4 probes (see composition in Table 6); the IC was then added to the mix to create a final IC concentration of 84 copies/reaction. To each well in the plate was added 47.5 µl of the final mix. Finally, 2.5 µl of the eluates from 24 CTSW deletion variant was added to the wells, such that each eluate was subjected to the reaction conditions individually. The reaction plate was sealed and then placed into an Abbott m2000rt cycler/reader and subjected to cycling conditions.

For every sample, a CY5™ signal was detected, indicating that the primers having the sequence of SEQ ID NOs:1 and 2 amplified the target region of the CTSW strain plasmids and was detected by the probe having the sequence of SEQ ID NO:3 that had been labeled with CY5™. The negative controls (containing no template) showed no signal, suggesting that the amplification was specific. All samples generated valid IC responses.

Example 3

Assessment of Potential Impact on Amplification of Current CT, NG and IC Targets The purpose of this example was to demonstrate that the primers having the sequence of SEQ ID NOs:1 and 2, combined with the probe having the sequence of SEQ ID NO:3, and primers having the sequence of SEQ ID NOs:14 and 15, combined with the probe having the sequence of SEQ ID NO:3 do not interfere with currently used primers and probes in a commercialized version of non-CTSW CT and NG detection.

Three master mixes were formulated, each sufficient for 48 reactions. Mix 0 (MM0) contained only the commercially available CT and NG primers and probes (see Table 4). Two other mixes had the CT and NG primers and probes and were spiked with one of the two sets of candidate CT primers and probe. Mix 1 (MM1) had SEQ ID NOs:1, 2 (CTSW primers) and 3 (CTSW probe), and Mix 4 (MM4) had SEQ ID NOs:14, 15 (CTSW primers) and 3 (CTSW probe). The candidate probes were labeled at the 5' end with QUASAR™ Q670 and the quencher BHQ-2™ at the 3' end. The concentrations for primers and probes are as noted in Table 5. IC was added to each mix to create a final IC concentration of 84 copies/reaction. CT/NG cutoff control from the commercially available REALTIME™ CT/NG Control Kit (Abbott Laboratories) was tested as sample for all three mixes.

The samples were loaded into the optical reaction plate and sealed. The plate was then loaded into the cycler/reader device and subjected to cycling conditions as specified in Example 2.

The addition of the SEQ ID NO:3 probe and SEQ ID NOs:1, 2, 14 and 15 primers did not effect amplification of the targets (current CT, NG or IC targets) because the difference in the detected signal between Mix 0 and Mixes 1 and 4 did not significantly differ.

Example 4

Assessment of Potential for Introducing Non-Specific Amplification

In this experiment, the hypothesis that the negative controls are not amplified by the primers/probe of the invention was tested.

A master mix (MM1) was prepared by spiking commercially available CT/NG reaction mix with SEQ ID NOs:1 and 2, combined with the probe having the sequence of SEQ ID NO:3. The SEQ ID NO:3 CT probe was labeled at the 5' end with QUASAR™ Q670 and the quencher BHQ-2™ at the 3' end. The concentrations for primers and probes are as noted in Table 6. IC was added to each mix to create a final IC concentration of 84 copies per reaction.

Negative diluent was tested as negative samples at 94 replicates per PCR sample plate along with two replicates of the positive controls. Positive controls were prepared from a dilution of a CT genomic DNA preparation and 25 µl of CT genomic-positive preparations. The samples were loaded into the optical reaction plate and sealed. The plate was then loaded into the cycler/reader device and subjected to cycling conditions as specified in Example 2. The plate was then analyzed for fluorophore signal, analyzing for FAM™, VIC™ and CY5™. The results are shown below in Table 7.

TABLE 7

Results from experiments testing for non-specific amplification

| Run | FAM ™ | VIC ™ | CY5 ™ |
|---|---|---|---|
| 1 | 94/94 not reactive | 1/94 slightly elevated, 93/94 not reactive | 94/94 not reactive |
| 2 | 94/94 not reactive | 1/94 reactive MR ~0.17 FCN ~41, 1/94 slightly elevated, 92/94 not reactive | 1/94 slightly elevated, 1/94 reactive MR ~0.16 FCN ~41, 92/94 not reactive |
| 3 | 1/94 reactive MR ~0.1 FCN ~40; 93/94 not reactive | 94/94 not reactive | 94/94 not reactive |
| 4 | 94/94 Not reactive | 1/94 elevated; 93/94 not reactive | 94/94 not reactive |
| 5 | 1/94 elevated; 93/94 not reactive | 94/94 not reactive | 94/94 not reactive |
| 6 | 94/94 not reactive | 94/94 not reactive | 94/94 not reactive |
| 7 | 94/94 not reactive | 94/94 not reactive | 94/94 not reactive |

Sporadic, low level CT FAM™, NG VIC™ and CT CY5™ signals were observed in runs 1-3, as shown in Table 7. To ascertain if there was contamination contributed from the laboratory environment, all laboratory benches were washed with bleach, and the experiment repeated four more times (runs 4-7 in Table 7). Out of a total of 376 replicates of negative samples (runs 4-7), one replicate showed low level late amplification in FAM™ and another replicate showed low-level, late amplification in VIC™. All other replicates produced no amplification signal in all three channels (FAM™, VIC™ and CY5™). Both incidences of low-level amplification had late cycle number calls and would not have been reported as positive by the commercially available REALTIME™ CT/NG assay. The positive controls produced valid positive amplification curves.

Except for some sporadic, low-level signal, all repetitions of the negative controls produced no signal in all three channels. Thus, the addition of the primers having the sequence of SEQ ID NOs:1 and 2 and the probe having the sequence of SEQ ID NO:3 to the CT/NG oligonucleotide reagent mix Table 4) did not cause elevated signal in any of the channels.

Example 5

Assessing Potential Difference in Detection of Low Level CT Targets Between the Original and the New Candidate Primer/Probe Set In this example, the primer/probe set having the sequences of SEQ ID NOs:1-3 was tested for sensitivity using three different dilutions of CT genomic DNA preparation DNA diluted in TE pH 8.0 and salmon testes DNA as a carrier). The relative dilutions were at 1, 1:7.5 and 1:50, creating samples mimicking low levels of CT from patient samples.

A master mix (MM1) was prepared by spiking commercially available CT/NG PCR reaction mix (Table 4) with SEQ ID NOs:1 and 2, combined with the probe having the sequence of SEQ ID NO:3. The SEQ ID NO:3 CT probe was labeled at the 5' end with QUASAR™ Q670 and the quencher BHQ-2™ at the 3' end. The concentrations for primers and probes were as noted in Table 6. IC was added to each mix to create a final IC concentration of 84 copies per reaction. The samples were loaded into the optical reaction plate and sealed. The plate was then loaded into the cycler/reader device and subjected to cycling conditions as specified in Example 2. The plate was then analyzed for fluorophore signal (FAM™ and CY5™). The results are shown below in Tables 8 and 9.

TABLE 8

Cycle number calls for 1x dilution of CT genomic DNA preparation

| | Channel: | | | |
|---|---|---|---|---|
| | FAM ™ | | CY5 ™ | |
| Condition | Mean cycle number (n = 28) | SD | Mean cycle number (n = 28) | SD |
| Bottle 1 | 34.91 | 0.151 | 34.22 | 0.152 |
| Bottle 2 | 35.09 | 0.179 | 34.32 | 0.184 |
| Grand Mean | 35.00 | | 34.27 | |

TABLE 9

Mean difference in cycle number between more diluted and 1x dilution of CT genomic DNA

| | Bottle 1 | Bottle 2 |
|---|---|---|
| FAM ™ (1:7.5 target dilution) | 2.69 | 2.82 |
| CY5 ™ (1:7.5 target dilution) | 2.68 | 2.87 |
| FAM ™ (1:50 target dilution) | 3.90 | 4.04 |
| CY5 ™ (1:50 target dilution) | 3.89 | 4.29 |

Bottles 1 and 2 were two different manual preparations of the same MM1 master mix. As shown in Table 8, little difference was observed between the two bottles on the mean cycle number calls for both FAM™ and CY5™. A slight delay was observed for the mean cycle number in FAM™ as compared to the CY5™ channel. For the more diluted samples of CT genomic DNA preparation, Table 9 shows the mean difference in cycle number between 1:7.5 or 1:50 dilution and that of 1x dilution. The each case, Table 9 shows that a slight delay of cycle number was observed in bottle 2 in both the FAM™ and CY5™ channels. Therefore, at each target levels, regardless of the dilution, assay performance was similar, regardless of the label (FAM™, CY5™).

Example 6

Detection of all CT Serovars

Having demonstrated that the primer/probe combination having the sequences of SEQ ID NOs:1-3 are sensitive and specific on control templates, the ability of the primer/probe combination to detect CT in different serovars (CT that differ in their protein composition as expressed on their cell surfaces) was tested. Sixteen serovars were tested at 100 copies/reaction and compared to negative controls. If the primer/probe combination amplified and detected the target region of the serovars, a signal is generated; otherwise, only background signal equal to that generated by the negative controls would be observed.

Two master mixes were formulated: Mix0 contained only the commercially available CT and NG primers and probes (Table 4), whereas MM1 was prepared by spiking commercially available CT/NG reaction mix with SEQ ID NOs:1 and 2, combined with the probe having the sequence of SEQ ID NO:3. The SEQ ID NO:3 CT probe was labeled at the 5' end with QUASAR™ Q670 and the quencher BHQ-2™ at the 3' end. The concentrations for primers and probes were as shown in Table 6. IC was added to each mix to create a final IC concentration of 84 copies/reaction. The samples were loaded into the optical reaction plate and sealed. The plate was then loaded into the cycler/reader device and subjected to cycling conditions as specified in Example 2. The plate was then analyzed for fluorophore signal (FAM™ and CY5™).

Signal was observed in all samples containing the different CT serovar DNA, while the negative controls showed no signal. Therefore, the primer/probe combination having the sequence of SEQ ID NOs:1-3 detected all 16 tested serovars.

Example 7

Screening Using a Panel of Potential Cross-Reactors

In this example, cross reactivity of the primer/probe set having the sequences of SEQ ID NOs:1-3 (MM1, as in Example 6) was tested. The performance of each sets of primers were tested with 107 potential cross-reacting organisms. The strains were collected as CT/NG REALTIME™ PCR assay cross-reactivity panels.

The list of potential cross-reacting organisms ("cross-reactors") is shown below in Table 10.

TABLE 10

Tested potential cross-reactors

| ID | Strain Name |
|---|---|
| 001 | *Achromobacter xerosis* |
| 002 | *Acinetobacter calcoaceticus* |
| 003 | *Acinetobacter lwoffii* |
| 004 | *Actinomyces israelii* |
| 005 | *Aerococcus viridans* |
| 006 | *Aeromonas hydrophila* |
| 007 | *Alcaligenes faecalis* |
| 008 | *Arcanobacterium pyogenes* |
| 009 | *Bacillus subtilis* |
| 010 | *Bacteroides fragilis* |
| 011 | *Bacteroides ureolyticus* |
| 012 | *Bifidobacterium adolescentis* |
| 013 | *Bifidobacterium breve* |
| 014 | *Brevibacterium linens* |
| 015 | *Campylobacter jejuni* |
| 016 | *Candida albicans* |
| 017 | *Candida glabrata* |
| 018 | *Candida parapsilosis* |
| 019 | *Candida tropicalis* |
| 020 | *Chlamydia psittaci* |
| 021 | *Chlamydia pneumoniae* |
| 022 | *Chromobacterium violaceum* |
| 023 | *Chryseobacterium meningosepticum* |
| 024 | *Citrobacter freundii* |
| 025 | *Clostridium sporogenes* |
| 026 | *Corynebacterium genitalium* |
| 027 | *Corynebacterium xerosis* |
| 028 | *Cryptococcus neoformans* |
| 029 | *Cytomegalovirus* |
| 030 | *Deinococcus radiodurans* |
| 031 | *Derxia gummosa* |
| 032 | *Eikenella corrodens* |
| 033 | *Enterobacter cloacae* |
| 034 | *Enterobactor aerogenes* |
| 035 | *Enterococcus avium* |
| 036 | *Enterococcus faecalis* |
| 037 | *Enterococcus faecium* |
| 038 | *Escherichia coli* |
| 039 | *Fusobacterium nucleatum* |
| 040 | *Gardnerella vaginalis* |
| 041 | *Gemella haemolysans* |

TABLE 10-continued

Tested potential cross-reactors

| ID | Strain Name |
|---|---|
| 042 | *Haemophilus ducreyi* |
| 043 | *Haemophilus influenzae* |
| 044 | *Helicobacter pylori* |
| 045 | *Herpes Simplex Virus, type I* |
| 046 | *Herpes Simplex Virus, type II* |
| 047 | *Human Papilloma Virus 16* |
| 048 | *Human Papilloma Virus 18* |
| 049 | *Kingella dentrificans* |
| 050 | *Kingella kingae* |
| 051 | *Klebsiella oxytoca* |
| 052 | *Klebsiella pneumoniae* |
| 053 | *Lactobacillus acidophilus* |
| 054 | *Lactobacillus brevis* |
| 055 | *Lactobacillus delbrueckii* subsp. *lactis* |
| 056 | *Lactobacillus jensonii* |
| 057 | *Legionella pneumophila* |
| 058 | *Listeria monocytogenes* |
| 059 | *Micrococcus luteus* |
| 060 | *Mobiluncus mulieris* |
| 061 | *Moraxella* (Branhamella) *catarrhalis* |
| 062 | *Moraxella lacunata* |
| 063 | *Moraxella osloensis* |
| 064 | *Morganella morganii* |
| 065 | *Mycobacterium gordonae* |
| 066 | *Mycobacterium smegmatis* |
| 067 | *Mycoplasma genitalium* |
| 068 | *Mycoplasma hominis* |
| 069 | *Neisseria flava* |
| 070 | *Neisseria meningitides*-A |
| 071 | *Neisseria meningitides*-B |
| 072 | *Neisseria meningitides*-C |
| 073 | *Neisseria meningitides*-D |
| 074 | *Neisseria perflava* |
| 075 | *Pantoea agglomerans* |
| 076 | *Peptostreptococcus anaerobius* |
| 077 | *Plesiomonas shigelloides* |
| 78 | *Proteus mirabilis* |
| 79 | *Proteus vulgaris* |
| 80 | *Providencia stuartii* |
| 81 | *Pseudomonas aeruginosa* |
| 82 | *Pseudomonas putida* |
| 83 | *Rahnella aquatilis* |
| 84 | *Rhizobium radiobacter* |
| 85 | *Rhodospirillum rubrum* |
| 86 | *Ruminococcus productus* |
| 87 | *Salmonella Minnesota* (choleraesnis) |
| 88 | *Salmonella typhimurium* |
| 89 | *Serratia marcescens* |
| 90 | *Staphylococcus aureus* |
| 91 | *Staphylococcus epidermidis* |
| 92 | *Staphylococcus saprophyticus* |
| 93 | *Streptococcus agalactiae* |
| 94 | *Streptococcus bovis* |
| 95 | *Streptococcus mitis* |
| 96 | *Streptococcus mutans* |
| 97 | *Streptococcus pneumoniae* |
| 98 | *Streptococcus pyogenes* |
| 99 | *Streptococcus salivarius* |
| 100 | *Streptococcus sanguinis* |
| 101 | *Streptomyces griseinus* |
| 102 | *Trichomonas vaginalis* |
| 103 | *Ureaplasma urealyticum* |
| 104 | *Veillonella parvula* |
| 105 | *Vibrio parahaemolyticus* |
| 106 | *Weissella ramensenteroides* |
| 107 | *Yersinia enterocolitica* |

The SEQ ID NO:3 CT probe was labeled at the 5' end with QUASAR™ Q670 and the quencher BHQ-2™ at the 3' end. The concentrations for primers and probes are as noted in Table 6. IC was added to each mix to create a final IC concentration of 84 copies/reaction. Twenty-five µl of master mix and 25 µl of negative diluent was added to each well that was designated for potential cross-reactor samples or negative controls. To those wells designated as a potential cross-reactor sample, 1 µl of the cross-reactor DNA sample was added (each cross-reactor of n=3), and 25 µl of CT genomic DNA was added to those wells that were used for positive controls. The tray was sealed and then loaded into an Abbott m2000rt cycler/reader and subjected to cycling conditions as specified in Example 2. The plate was then analyzed for fluorophore signal (FAM™ and CY5™).

All potential cross reactors were not reactive except the five strains shown below in Table 11, which exhibited elevated VIC™ signal. Each sample was tested at $2\times10^6$ molecules/reaction.

TABLE 11

Cross-reacting strains testing at $2 \times 10^6$ molecules per reaction

| ID | CY5™ Results | VIC™ Results | FAM™ Results |
|---|---|---|---|
| 10 | NR | 1/3 reactive w/MRB ~0.14, FCNB ~37-38 | NR |
| 21 | NR | 3/3 reactive w/ MRB ~0.14-0.15, FCNB ~37-38 | NR |
| 70 | NR | 3/3 reactive w/ MRB ~0.15, FCNB ~35 | NR |
| 71 | NR | 3/3 reactive w/ MRB ~0.15, FCNB ~36-37 | NR |
| 89 | NR | 2/3 reactive w/ MRB ~0.09, FCNB ~39, 1/3 wells with MRB ~0.11, FCNB ~43 | NR |

NR, not reactive
MRB and FCNB are maximum ratio and fractional cycle number, respectively. Both are outputs of curve shape analysis of PCR amplification.

The strains listed in Table 11 were then subjected to another round of testing to compare with the reagents for MM0 and MM1 (as in Example 6). These strains were tested at $1\times10^6$ and $3.3\times10^5$ molecules/reaction. The results of this second set of testing are shown below in Table 12.

TABLE 13

Primer (SEQ ID NOs: 1, 2) and probe (SEQ ID NO: 3) concentrations in assayed master mixes (MMs)

| | SEQ ID NO: 1 | SEQ ID NO: 2 | SEQ ID NO: 3 |
|---|---|---|---|
| "Nominal" | 500 nM | 500 nM | 200 nM |
| MM1 | 250 nM | 250 nM | 200 nM |
| MM2 | 375 nM | 375 nM | 200 nM |
| MM3 | 625 nM | 625 nM | 200 nM |
| MM4 | 750 nM | 750 nM | 200 nM |
| MM5 | 375 nM | 500 nM | 200 nM |
| MM6 | 625 nM | 500 nM | 200 nM |
| MM7 | 500 nM | 375 nM | 200 nM |
| MM8 | 500 nM | 625 nM | 200 nM |
| MM9 | 500 nM | 500 nM | 150 nM |
| MM10 | 500 nM | 500 nM | 250 nM |

The target consisted of a CT genomic DNA preparation diluted 1:7.5 as in Example 4. Twenty-five µl of master mix and 25 µl of target was added to each well. The tray was sealed and then loaded into an Abbott m2000rt cycler/reader and subjected to a cycle of 95° C. for 570 seconds, and then 45 cycles of 92° C. for 10 seconds, 58° C. for 30 seconds, and 65° C. for 60 seconds. The plate was then analyzed for fluorophore signal (FAM™ and CY5™).

The results showed that, in the CY5™ channel, FCN was slightly later with MM1 (−25% for both primers (SEQ ID NOs:1, 2) than in nominal condition. FCN was slightly earlier with MM4 (+50% both primers) when compared to the nominal condition, indicating a slightly more efficient amplification. Overall, all master mixes were comparable with the nominal condition. For IC, FCN and MR were comparable

TABLE 12

Results from re-assay of potential cross-reacting strains

| Strain ID | MM0 CY5™ | MM0 VIC™ | MM0 FAM™ | MM1 CY5™ | MM1 VIC™ | MM1 FAM™ |
|---|---|---|---|---|---|---|
| 10 | NR | NR | NR | NR | $1 \times 10^6$: 2/3 Reactive; MRB ~0.08-0.1, FCNB ~40; $3.3 \times 10^5$: 3/3 NR | NR |
| 21 | NR | $1 \times 10^6$: 3/3 Reactive; MRB ~0.13-0.15, FCNB ~37-39; $3.3 \times 10^5$: 1/3 Reactive; MRB ~0.12, FCNB ~42 | NR | NR | $1 \times 10^6$: 2/3 Reactive; MRB ~0.14-0.15, FCNB ~39-41; $3.3 \times 10^5$: 2/3 Reactive; MRB 0.14, 0.07, FCNB 40, 44 | NR |
| 70 | NR | $1 \times 10^6$: 3/3 Reactive; MRB ~0.15, FCNB ~36; $3.3 \times 10^5$: 2/3 Reactive MRB ~0.12-0.15, FCNB ~39-40 | NR | NR | $1 \times 10^6$: 3/3 Reactive; MRB~−0.15 FCNB ~36; $3.3 \times 10^5$: 2/3 Reactive; MRB 0.14-0.15, FCNB 36-37 | NR |
| 71 | NR | $1 \times 10^6$: 3/3 Reactive; MRB ~0.13-0.15, FCNB ~37-39; $3.3 \times 10^5$: 2/3 reactive; MRB 0.12-0.13, FCNB ~36-37 | NR | NR | $1 \times 10^6$: 3/3 Reactive; MRB~−0.15 FCNB ~37; $3.3 \times 10^5$: 2/3 Reactive; MRB 0.1, 0.13, FCNB 39, 41 | NR |

NR, not reactive

As shown in Table 12, the results from both the MM0 and MM1 reagents were comparable except for strain ID 10, which was non-reactive with MM0.

Example 8

Guardband Study

In this study, SEQ ID NOs:1-3 were titrated against each other to ascertain optimal concentrations. Table 13 shows the different master mixes (MMs) used in this study, indicating the various concentrations of the primers and probe. IC was added to each mix to create a final IC concentration of 84 copies/reaction.

across all master mix conditions compared with the nominal condition. FCN and MR were identical to FCNB and MRB for all the positive samples (Table 13).

Example 9

Testing of Patient Samples and Comparison of Amplification in FAM™ (Original Set) and CY5™ (New Set) Channels In this example, MM1 master mix (see Example 6) containing SEQ ID NOs:1-3 was tested on human subject urine samples with m2000 experimental application specification file on m2000sp and m2000rt. In total, 43 urine samples were tested. The sample preparation portion of the m2000 experimental application specification file is a modification of the current on-market m2000 CT/NG application specification file version 2.00. The urine samples were collected in Abbott Multi-Collect transport tube for Abbott under Internal Review Board-approved protocols and with patient consent. PCR plate was prepared on m2000sp and then transferred to m2000rt for PCR amplification and detection. The cycling conditions were as described in Example 2. The m2000rt detection portion of this experimental application specification file differed from the current on-market m2000 CT/NG application specification file version 2.00 in that detection in CY5™ channel was added. The results were then to compared with the results on these same urine samples prepared from an identical sample preparation protocol (CT/NG experimental application specification file v0.24) and tested with the current on-market m2000 CT/NG assay reagents (MM0, Example 6).

Twenty-five μl of master mix and 25 μl of urine sample preparation was added to each well. The concentrations for primers and probes were as noted in Table 6. The tray was sealed and then loaded into an Abbott m2000rt cycler/reader and subjected to a cycle of 95° C. for 570 seconds, and then 45 cycles of 92° C. for 10 seconds, 58° C. for 30 seconds, and 65° C. for 60 seconds. The plate was then analyzed for fluorophore signal (FAM™ and CY5™).

Both m2000sp and m2000rt runs were successful. All the samples results from MM1 correlated well with those from previously tested MM0 with the exception of urine sample #114. This sample was previously reported as negative with MM0 but showed late amplification with MM1 in CY5™ channel. A review of MM0 testing data on the swab sample taken from the same subject showed that swab test was positive. Therefore, urine sample #114 was likely a true low positive CT sample and that the amplification observed in CY5™ channel on this sample is likely specific for CT Example 10

Probe Labeling for Providing a Single CT Result

In this example, SEQ ID NO:3 was labeled with FAM™. In this configuration, only one CT result is given, regardless if CT or CTSW is detected.

In the first part of this Example, a master mix was prepared for MM0 (Example 6), SEQ ID NOs:1, 2 (primers) and 3 (probe), and SEQ ID NOs:14, 15 primers) and 3 (probe). The probe for SEQ ID NO:3 was labeled at the 5' end with FAM™ and the quencher BHQ-1™ at the 3' end. The concentrations for primers and probes are as noted in Table 5. IC was added to each mix to create a final IC concentration of 84 copies/reaction. The mixes were tested at four target levels: (1) a 1×CT genomic DNA preparation; (2) 1:7.5 dilution; and (3) a 1:50 dilution of this same preparation (1-3 as for Example 4) and (4) a negative control. The concentrations for primers and probes were as noted in Table 6.

In the second part of this example, master mixes containing (1) CT/NG reagents (MM0); (2) MM1 (SEQ ID NOs:1, 2 and 3; 3 being labeled with FAM™) and (3) SEQ ID NOs:13, 15 and SEQ ID NO:3, again labeled with FAM™ (MM4) were tested in two PCR plates. The first plate contained CT/NG cutoff control and three dilutions of CT genomic DNA targets (see Example 4) and the second used CTSW DNA preparations as a target (diluted 1:100, 1:200, 1:400, and 1:800 from eluate of one clinical sample as in Example 2). The concentrations for primers and probes are as noted in Table 5. MM4 was the same as MM1, except the primers were SEQ ID NOs:13 and 15.

After loading the samples into the tray and sealing the tray, it was then loaded into an Abbott m2000rt cycler/reader and subjected to a cycle of 95° C. for 570 seconds, and then 45 cycles of 92° C. for 10 seconds, 58° C. for 30 seconds, and 65° C. for 60 seconds. The plate was then analyzed for fluorophore signal (FAM™ and CY5™).

At all target levels with SEQ ID NO:3 as a FAM™ probe, regardless of target, primers of SEQ ID NOs:1 and 2 were slightly more "robust" than primers of SEQ ID NOs:13 and 15.

REFERENCES

Abravaya, K., J. Hackett Jr, S. Huang, K.-C. Luk, J. Salituro, and L. Morrison. 2005. DOUBLE STRANDED LINEAR NUCLEIC ACID PROBE AND USES THEREOF. US Patent Application Publication No. 20050227257.

Ausubel, F. M., R. Brent, R. E. Kingston, D. D. Moore, J. G. Seidman, J. A. Smith, and K. Struhl. 1987. *Current protocols in molecular biology*. John Wiley & Sons, New York.

Black, C. M., J. E. Johnson, C. E. Farshy, T. M. Brown, and B. P. Berdal. 1991. Angenic variation among strains of *Chlamydia pneumoniae*. *J Clin Microbiol*. 29:1312-6.

Buchardt, O., P. E. Nielsen, and R. H. Berg. 1992. PEPTIDE NUCLEIC ACIDS. WO 92/20702.

Comanducci, M., S. Ricci, R. Cevenini, and G. Ratti. 1990. Diversity of the *Chlamydia trachomatis* common plasmid in biovars with different pathogenicity. *Plasmid*. 23:149-54.

Fino, J. 1995. HAPTENS, TRACERS, IMMUNOGENS AND ANTIBODIES FOR CARBAZOLE AND DIBENZOFURAN DERIVATIVES. U.S. Pat. No. 5,464,746.

Gelfand, D., P. Holland, R. Saiki, and R. Watson. 1993. U.S. Pat. No. 5,210,015.

Jalal, H., H. Stephen, M. D. Curran, J. Burton, M. Bradley, and C. Carne. 2006. Development and validation of a rotor-gene real-time PCR assay for detection, identification, and quantification of *Chlamydia trachomatis* in a single reaction. *J Clin Microbiol*. 44:206-13.

Marras, S. A., F. R. Kramer, and S. Tyagi. 1999. Multiplex detection of single-nucleotide variations using molecular beacons. *Genet Anal*. 14:151-6.

Mattingly, P. 1995. HAPTENS, TRACERS, IMMUNOGENS AND ANTIBODIES FOR 3-PHENYL-A-ADAMANTANEACETIC ACIDS. U.S. Pat. No. 5,424,414.

Ngeow, Y. F. 1996. Limitations of serodiagnosis in chlamydial genital tract infections. *Ann Acad Med Singapore*. 25:300-4.

Nielsen, P. E., M. Egholm, R. H. Berg, and O. Buchardt. 1991. Sequence-selective recognition of DNA by strand displacement with a thymine-substituted polyamide. *Science*. 254:1497-500.

Pabich, E., R. Marshall, and H. Yu. 2004. POLYNUCLEOTIDES FOR THE AMPLIFICATION AND DETECTION OF *CHLAMYDIA TRACHOMATIS* AND *NEISSERIA GONORRHOEAE*. Patent Application Publication No. US 2004/0091870.

Palmer, L., and S. Falkow. 1986. A common plasmid of *Chlamydia trachomatis*. *Plasmid*. 16:52-62.

Pandian, S., E. Aw, and D. Smith. 1997. METHOD OF AMPLIFICATION FOR INCREASING THE SENSITIVITY OF DETECTING NUCLEIC ACID-PROBE TARGET HYBRIDS. U.S. Pat. No. 5,627,030.

Pickett, M. A., J. S. Everson, P J. Pead, and I. N. Clarke. 2005. The plasids of *Chlamydia trachomatis* and *Chlamydophila pneumoniae* (N16): accurate determination of copy number and the paradoxical effect of plasmid-curing agents. *Microbiology.* 151:893-903.

Ripa, T., and P. Nilsson. 2006. A variant of *Chlamydia trachomatis* with deletion in cryptic plasmid: implications for use of PCR diagnostic tests. *Euro Surveill.* 11:E0611092.

Ruth, J. 1990. SINGLE-STRANDED LABELLED OLIGO-NUCLEOTIDES, REACTIVE MONOMERS AND METHODS OF SYNTHESIS. U.S. Pat. No. 4,948,882.

Tam, J. E., C. H. Davis, R. J. Thresher, and P. B. Wyrick. 1992. Location of the origin of replication for the 7.5-kb *Chlamydia trachomatis* plasmid. *Plasmid.* 27:231-6.

Tyagi, S., D. P. Bratu, and F. R. Kramer. 1998. Multicolor molecular beacons for allele discrimination. *Nat Biotechnol.* 16:49-53.

van der Mol, A. R., J. N. Mol. and A. R. Stuitje. 1988. Modulation of eukaryotic gene expression by complementary RNA or DNA sequences. *Biotechniques.* 6:958-76.

Zon, G. 1988. Oligonucleotide analogues as potential chemotherapeutic agents. *Pharm Res.* 5:539-49.

We claim:

1. A set of polynucleotides comprising a first, a second, and a third isolated polynucleotide, wherein
    the first polynucleotide consists of SEQ ID NO: 1, or the complement thereof, wherein the complement is identical in length to SEQ ID NO: 1;
    the second polynucleotide consists of SEQ ID NO: 2, or the complement thereof, wherein the complement is identical in length to SEQ ID NO: 2; and
    the third polynucleotide consists of SEQ ID NO:3, or the complement thereof, wherein the complement is identical in length to SEQ ID NO:3, and wherein the third polynucleotide comprises a label and a quencher.

2. The polynucleotide set of claim 1, further comprising a fourth, a fifth and a sixth isolated polynucleotide, wherein
    the fourth polynucleotide consists of SEQ ID NO: 28, or the complement thereof, wherein the complement is identical in length to SEQ ID NO: 28;
    the fifth polynucleotide consists of SEQ ID NO: 31, or the complement thereof, wherein the complement is identical in length to SEQ ID NO: 31; and
    the sixth polynucleotide consists of SEQ ID NO: 33, or the complement thereof, wherein the complement is identical in length to SEQ ID NO: 33.

3. The polynucleotide set of claim 2, wherein the sixth polynucleotide comprises a label and a quencher.

4. A kit, comprising the polynucleotide set of claim 1 and amplification reagents.

5. A method of amplifying a *Chlamydia trachomatis* nucleic acid sequence in a sample, comprising (a) forming a reaction mixture comprising amplification reagents, a sample suspected of containing a *Chlamydia trachomatis* nucleic acid sequence and the set of polynucleotides of claim 1; and
   (b) subjecting the reaction mixture to conditions to promote the amplification reagents to amplify at least one copy of a nucleic acid sequence complementary to the third polynucleotide.

6. The method of claim 5, wherein the reaction mixture further comprises a control target polynucleotide and a control polynucleotide probe.

7. A method of detecting *Chlamydia trachomatis* in a sample, comprising
   (a) forming a reaction mixture comprising amplification reagents, a sample suspected of containing a *Chlamydia trachomatis* nucleic acid sequence and the set of polynucleotides of claim 1;
   (b) subjecting the reaction mixture to conditions to promote the amplification reagents to amplify at least one copy of a nucleic acid sequence complementary to the third polynucleotide;
   (c) subjecting the reaction mixture to conditions to promote specific hybridization of the third polynucleotide to a target sequence; and
   (d) detecting third polynucleotide:target sequence hybrids.

8. The method of claim 7, wherein the reaction mixture further comprises a control target polynucleotide and a control polynucleotide probe.

* * * * *